United States Patent
Yan et al.

(10) Patent No.: US 8,927,510 B2
(45) Date of Patent: Jan. 6, 2015

(54) COMPOSITIONS AND METHODS FOR INHIBITION OF RETROVIRUSES

(75) Inventors: Nan Yan, Boston, MA (US); Alan Engelman, Brookline, MA (US); Judy Lieberman, Brookline, MA (US)

(73) Assignees: Children's Medical Center Corporation, Boston, MA (US); Dana-Farber Cancer Institute, Inc., Boston, MA (US)

( * ) Notice: Subject to any disclaimer, the term of this patent is extended or adjusted under 35 U.S.C. 154(b) by 690 days.

(21) Appl. No.: 12/992,797

(22) PCT Filed: May 18, 2009

(86) PCT No.: PCT/US2009/044339
§ 371 (c)(1),
(2), (4) Date: Feb. 9, 2011

(87) PCT Pub. No.: WO2009/140676
PCT Pub. Date: Nov. 19, 2009

(65) Prior Publication Data
US 2011/0142854 A1    Jun. 16, 2011

Related U.S. Application Data

(60) Provisional application No. 61/053,769, filed on May 16, 2008.

(51) Int. Cl.
*C12N 15/11*    (2006.01)
*A61K 31/00*    (2006.01)

(52) U.S. Cl.
CPC ....... *A61K 31/00* (2013.01); *C12N 2740/16011* (2013.01); *A81K 31/7105* (2013.01)
USPC ...................................... 514/44 A

(58) Field of Classification Search
USPC ...................................................... 514/44 A
See application file for complete search history.

(56) References Cited

U.S. PATENT DOCUMENTS

2003/0229004 A1    12/2003    Zarling et al.

FOREIGN PATENT DOCUMENTS

WO    WO99/61064    *    2/1999
WO    2006002971 A2    1/2006

OTHER PUBLICATIONS

Chou, K.M., et al, "An exonucleolytic activity of human apurinic/apyridiminic endonuclease on 3' mispaired DNA," Nature, Feb. 7, 2002, vol. 415, No. 6872, pp. 655-659.
Ott, D.E., et al., "Actin-binding cellular proteins inside human immunodeficiency virus type I," Virology, Jan. 5, 2000, vol. 266, No. 1, pp. 42-51.
Hindmarsh, P., et al., "HMG protein family members stimulate human immunodeficiency virus type 1 and avian sarcoma virus concerted DNA integration in vitro," J. Virol., Apr. 1999, vol. 73, No. 4, pp. 2994-3003.
Chowdhury, D. et al., "Death by a thousand cuts: granzyme pathways of programmed cell death," Annu. Rev. Immunol., Nov. 28, 2007, vol. 26. pp. 389-420.
Yan, N. et al., The SET complex acts as a barrier to autointegration of HIV-1, PLoS Pathog., Mar. 6, 2009, vol. 5, No. 3, e1000327.

* cited by examiner

*Primary Examiner* — Brian Whiteman
(74) *Attorney, Agent, or Firm* — Mark J. FitzGerald; David S. Resnick; Ravinderjit Braich

(57) ABSTRACT

Described herein are methods and compositions for the inhibition of retroviral integration and replication. The methods and compositions inhibit the activity of one or more components of the SET complex or base excision repair enzymes and induce autointegration of retroviral double-stranded nucleic acid.

5 Claims, 9 Drawing Sheets

Control siRNA knockdown autointegration sites

| | -10 | -9 | -8 | -7 | -6 | -5 | -4 | -3 | -2 | -1 | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|---|---|---|---|---|---|---|---|---|
| A | 123 | 119 | 112 | 123 | 116 | 83 | 94 | 80 | 98 | 123 | 105 | 112 | 137 | 156 | | 90 | 112 | | 116 | 145 | 137 | 101 | 109 | 119 | 127 |
| T | 123 | 101 | 117 | 107 | 110 | 126 | 114 | | 150 | 120 | | 160 | 126 | 117 | 98 | 126 | 129 | 77 | 86 | 120 | 101 | 132 | 136 | 120 | 107 |
| G | 87 | 149 | 97 | 97 | 103 | 138 | 154 | 118 | 159 | 128 | | 87 | 57 | 87 | 113 | 87 | | 97 | 126 | 103 | 159 | 92 | 118 | 113 | 133 |
| C | 133 | 114 | 148 | 146 | 148 | 133 | 123 | 94 | | 99 | 148 | 89 | 109 | 99 | | | 148 | 153 | 163 | 94 | 79 | 143 | 99 | 118 | 109 |

SET/NM23-H1 siRNA knockdown autointegration sites

| | -10 | -9 | -8 | -7 | -6 | -5 | -4 | -3 | -2 | -1 | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|---|---|---|---|---|---|---|---|---|
| A | 104 | 94 | 102 | 89 | 92 | 64 | 89 | 67 | 77 | 109 | 87 | 92 | 74 | 139 | | 79 | 114 | 146 | 94 | 127 | 131 | 127 | 97 | 79 | 112 |
| T | 98 | 110 | 92 | 98 | 128 | 106 | 108 | 135 | 120 | 79 | | 139 | 112 | 106 | 79 | 84 | 120 | 55 | 86 | 67 | 69 | 86 | 104 | 100 | 100 |
| G | 112 | 89 | 92 | 109 | 92 | 129 | 89 | 119 | 172 | 155 | | 79 | 112 | 73 | 125 | 73 | | 86 | 106 | 96 | 99 | 76 | 125 | 122 | 86 |
| C | 87 | 102 | 117 | 108 | 75 | 106 | 111 | 72 | | 69 | 132 | 72 | 102 | 69 | | | 108 | 123 | 123 | 120 | 108 | 111 | 75 | 105 | 99 | position:

K

L  M  N

O

L

COMPOSITIONS AND METHODS FOR INHIBITION OF RETROVIRUSES

CROSS REFERENCE TO RELATED APPLICATIONS

This application is a 35 U.S.C. §371 National Phase Entry application of International Application No. PCT/US2009/044339 filed on May 18, 2009, which designates the United States, and which claims the benefit of priority under 35 U.S.C. §119(e) of the U.S. Provisional Application No. 61/053,769 filed May 16, 2008 the contents of which are herein incorporated by reference in their entirety.

SEQUENCE LISTING

The instant application contains a Sequence Listing which has been submitted in ASCII format via EFS-Web and is hereby incorporated by reference in its entirety. Said ASCII copy, created on Jan. 5, 2010, is named 33393623.txt and is 12,967 bytes in size.

FIELD OF INVENTION

The present invention relates generally to compositions and methods that can be used for the inhibition of retroviruses.

BACKGROUND OF THE INVENTION

Retroviruses are extremely successful pathogens affecting virtually all branches of life. These viruses are champions of persistence, and are maintained as proviral DNAs integrated into the genome of somatic cells and can even enter into the germ line. Infection can result in cell death, or in oncogenic transformation by insertional mutagenesis. Thus, there is tremendous evolutionary selective pressure to block or prevent retrovirus replication. In recent years, it has become apparent that mammalian cells have evolved a number of powerful mechanisms to limit or restrict virus replication, constituting novel aspects of intrinsic immunity. These mechanisms act at many diverse steps in the life cycle. The potential importance of these restriction factors is highlighted by the fact that many retroviruses, in turn, have evolved mechanisms to inactivate or overcome the blocks to infection (D. Wolf and S. P. Goff, 2008, Ann. Rev. Gen., 42: 143-163).

Integration into the genome of the host cell is a defining feature of retroviral replication. Once integrated, the viral DNA is replicated along with cellular DNA during each cycle of cell division. The viral DNA is synthesized by reverse transcription of the viral RNA genome that enters the host cell upon infection. Reverse transcription takes place in the reverse transcription complex (RTC), a nucleoprotein complex that is derived from the core of the infecting virion. The newly synthesized viral DNA remains associated with viral and cellular proteins in a large nucleoprotein complex called the pre-integration complex (PIC). The viral integrase protein that integrates viral DNA into the host genome is one of the key components of the PIC. Reverse transcription occurs in the cytoplasm, so the PIC must be transported to the nuclear periphery and cross the nuclear envelope before integration of the viral DNA into the host chromosome. The size of the PIC, which is larger than a ribosome and much larger than a nuclear pore, excludes passive diffusion as a viable mechanism for translocation, and therefore active cellular transport mechanisms must be used for this task (Y. Suzuki and R. Craigie, 2007, Nat Rev Microbiol, 5:187-196).

The synthesis of full-length viral DNA in the RTC produces the PIC. The PIC efficiently integrates viral DNA into a target DNA in vitro and is the most extensively studied retroviral nucleoprotein complex. Both MoMLV and HIV-1 PICs are large complexes with a size comparable to (or greater than) ribosomes. Information on the protein composition of PICs is mostly restricted to immunoprecipitation studies and sensitive western-blot analyses because of the small quantity of material present in cell extracts. PICs retain many components of the RTC, but differences have been reported between HIV-1 and MoMLV. Some of these differences might reflect different PIC isolation protocols and the sensitivity of assays. Immunoprecipitation of MoMLV PICs detected CA and IN22, 27, whereas HIV-1 PICs were shown to contain nucleocapsid (NC), MA, RT, IN and Vpr. In addition to viral proteins, several cellular proteins, including barrier-to-autointegration factor (BAF), high-mobility group proteins (HMGs), Ku, lamina-associated polypeptide 2 (LAP2) and lens-epithelium-derived growth factor (LEDGF/p75), have been found associated with retroviral PICs.

The chromosomal DNA that serves as the target for retroviral DNA integration is enclosed by the nuclear envelope, which forms the boundary between the nucleus and cytoplasm, and separates nucleoplasmic and cytoplasmic enzymic activities. The nuclear envelope comprises two lipid bilayers: the outer and inner nuclear membranes. These membranes are separated by a lumen and joined at nuclear pore complexes (NPCs) that serve as a gate for traffic crossing the nuclear envelope. In dividing cells, breaking and re-forming of the nuclear envelope during each cycle of cell division allows a straightforward exchange of material between the nuclear and cytoplasmic compartments. Some retroviral PICs seem to take advantage of nuclear-envelope disassembly during cell division to gain access to chromatin. However, human immunodeficiency virus 1 (HIV-1) and other lentiviruses infect non-dividing cells and must therefore cross an intact nuclear envelope. The HIV-1 PIC must therefore carry karyophilic signals that direct transport across the intact nuclear envelope through NPCs.

The ability to infect non-dividing cells is not restricted to lentiviruses. However, recent data reveal that avian sarcoma virus (ASV) as well as Friend murine leukaemia virus (FrMLV) can infect non-dividing cells including growth-arrested cells, neurons and macrophages, albeit less efficiently than HIV-1. Cell-cycle-independent infection has been also proposed for other retroviruses, including HFV and spleen necrosis virus.

In the case of HIV-1, soon after HIV-1 enters a susceptible target cell, the viral genomic RNA is reverse transcribed within the reverse transcription complex (RTC) to double-stranded DNA (S. P. Goff, Nat Rev Microbiol 5, 253 (2007)). The RTC matures into the preintegration complex (PIC), which delivers the viral DNA to the nucleus for integration into a host chromosome (Y. Suzuki, R. Craigie, Nat Rev Microbiol 5, 187 (2007)). The PIC may also sequester and protect the viral DNA from cellular DNA-modifying enzymes (K. Yoder et al., Proc Natl Acad Sci USA 103, 4622 (2006)) and from cytoplasmic DNA sensors (R. Medzhitov, Nature 449, 819 (2007); A. Takaoka et al., Nature 448:501-505 (2007); D.B. Stestson Cell 134:587-598 (2008)) that could trigger antiviral innate immunity.

Relatively little is known about the host proteins that associate with the PIC and assist in retroviral, e.g., HIV-1, integration. Retroviral integration can be divided into three steps: (1) 3' processing (integrase (IN)-mediated hydrolysis of GT dinucleotides from HIV-1 DNA to produce reactive, recessed $CA_{OH}3'$ ends); (2) DNA strand transfer (IN-mediated insertion of the cleaved 3' ends into opposing strands of host chromosomal DNA); and (3) 5'-end joining (repair by host enzymes of the gaps between the 5'-ends of viral DNA and the chromosome) (A. Engelman, Curr Top Microbiol Immunol 281, 209 (2003)).

While the 3' processing of the viral DNA is required for host integration, 3'-processing also makes the viral DNA vulnerable to autointegration (C. Shoemaker et al., J Virol 40, 164 (1981); L. Li et al., J Virol 72, 2125 (1998)) in which the reactive CA ends attack sites within the viral DNA. Autointegration is mechanistically analogous to chromosomal integration, but results in nonproductive deletion or inversion circles of the viral DNA (Y. Li et al., J Virol 65, 3973 (1991); D. J. Garfinkel et al., J Virol 80, 11920 (2006); L. Li et al., J Virol 72, 2125 (1998); M. S. Lee and R. Craigie, Proc Natl Acad Sci USA 95, 1528 (1998)). Autointegration is a problem faced not only by retroviruses, but also by mobile genetic elements including bacteriophages and retrotransposons (D. J. Garfinkel et al., J Virol 80, 11920 (2006); H. W. Benjamin and N. Kleckner, Cell 59, 373 (1989); A. Maxwell et al., Proc Natl Acad Sci USA 84, 699 (1987)). Each such element employs a unique mechanism, relying on either self or host factors, to control autointegration. For example, bacteriophage Mu B protein activates DNA strand transfer to favor intermolecular transposition (A. Maxwell et al., Proc Natl Acad Sci USA 84, 699 (1987); K. Adzuma and K. Mizuuchi, Cell 57, 41 (1989)). In the case of Tn10, a cellular global regulator, H-NS, acts directly on the PIC to promote intermolecular transposition (S. J. Wardle et al., Genes Dev 19, 2224 (2005)). The barrier-to-autointegration factor (BAF) is a cellular protein that protects Moloney murine leukemia virus (MLV) PICs from autointegration and stimulates intermolecular integration in vitro (M. S. Lee and R. Craigie, Proc Natl Acad Sci USA 95, 1528 (1998); Y. Suzuki and R. Craigie, J Virol 76, 12376 (2002)). Although BAF can also stimulate HIV-1 PIC intermolecular integration activity in vitro, it has not been shown to block HIV-1 autointegration (M. C. Shun et al., J Virol 81, 166 (2007); J. M. Jacque and M. Stevenson, Nature 441, 641 (2006); H. Chen and A. Engelman, Proc Natl Acad Sci USA 95, 15270 (1998)).

Herein, we show that the SET complex plays an important role in the early phase of the retroviral lifecycle by inhibiting autointegration. Methods and compositions for inhibiting retroviral integration, and thus retroviral replication and spread of infections are described herein that exploit the identification of the role of the SET complex in preventing retroviral infection.

SUMMARY OF INVENTION

The inventors have surprisingly discovered that retroviruses utilize SET complex and base excision repair enzymatic activity to prevent autointegration of retroviral nucleic acid during the process of retroviral integration into a host genome. Thus, the inventors have discovered, in part, that inhibition of one or more components of the SET complex or base excision repair enzymes promotes retroviral autointegration and inhibits provirus formation. Accordingly, described herein are methods and compositions for promoting retroviral autointegration and inhibiting provirus formation.

One aspect of the present invention provides methods of increasing autointegration of a retroviral nucleic acids comprising contacting a cell infected with a retrovirus with an inhibitor of one or more components of the SET complex. Another aspect relates to methods of decreasing retroviral nucleic acid integration into a host cell genome comprising contacting a cell infected with a retrovirus with an inhibitor of one or more components of the SET complex. A further aspect of the invention relates to methods of inhibiting provirus formation in a cell comprising contacting a cell infected with a retrovirus with an inhibitor of one or more components of the SET complex. In some embodiments of this aspect and all aspects described herein, the component of the SET complex being inhibited is selected from selected from the group consisting of APE1, NM23-H1, TREX1, SET, HMGB2, and Pp32. In some embodiments of this aspect and all aspects described herein, the inhibitor of the SET complex is an antibody or antigen-binding fragment thereof, a small molecule, a peptide, or a nucleic acid. In some embodiments of this aspect and all aspects described herein, the inhibitor is a nucleic acid that comprises a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:9. In some embodiments of this aspect and all aspects described herein, the retrovirus is a lentivirus. In some embodiments of this aspect and all aspects described herein, the lentivirus is a human immunodeficiency virus (HIV). In some embodiments of this aspect and all aspects described herein, increases in autointegration are measured using other methods of the invention. For example, an embedded quantititave PCR assay to detect viral autointegration products in extrachromosomal cellular DNA fractions.

The invention also provides, in some aspects, methods of increasing autointegration of a retroviral nucleic acid comprising contacting a cell infected with a retrovirus with an inhibitor of one or more base excision repair enzymes. The invention also provides in one aspect methods of decreasing retroviral nucleic acid integration into a host cell genome comprising contacting a cell infected with a retrovirus with an inhibitor of one or more base excision repair enzymes. Another aspect provides methods of inhibiting provirus formation in a cell comprising contacting a cell infected with a retrovirus with with an inhibitor of one or more base excision repair enzymes. In some embodiments of this aspect and all aspects described herein, the base excision repair enzyme being inhibited is selected from the group consisting of OGG1, NTHL1, NEIL1, NEIL2, NEIL3, MUTYH, MPG, UNG, SMUG1, TDG, MBD4, APEX1, POLB, FEN1, XRCC1, and LIG3. In some embodiments of this aspect and all aspects described herein, the inhibitor of the base excision repair enzyme is an antibody or antigen-binding fragment thereof, a small molecule, a peptide, or a nucleic acid. In some embodiments of this aspect and all aspects described herein, the inhibitor is a nucleic acid comprising a sequence selected from the group consisting of SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14. In some embodiments of this aspect and all aspects described herein, the retrovirus is a lentivirus. In some embodiments of this aspect and all aspects described herein, the lentivirus is a human immunodeficiency virus (HIV). In some embodiments of this aspect and all aspects described herein, increases in autointegration are measured using other methods of the invention. For example, an embedded quantititave PCR assay to detect viral autointegration products in extrachromosomal cellular DNA fractions.

Another aspect of the present invention relates to methods for the treatment of a retroviral infection in a subject in need thereof comprising administering to a subject in need an effective amount of a composition comprising an inhibitor of one or more components of the SET complex. In some embodiments, the component of the SET complex being inhibited is selected from the group consisting of APE1, NM23-H1, TREX1, SET, HMGB2, and Pp32. In some embodiments of this aspect and all aspects described herein, the inhibitor of the SET complex is an antibody or antigen-binding fragment thereof, a small molecule, a peptide, or a nucleic acid. In some embodiments, the inhibitor is a nucleic acid that comprises a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:9. In some embodiments, the retrovirus is a lentivirus. In some embodiments, the lentivirus is a human immunodeficiency virus (HIV). Topical and systemic routes of administration are possible, e.g., oral, transmucosal, parenteral, nasal inhalation, intratracheal, intrathecal, intracranial, intramuscular, intraperitoneal, intracerebrospinal, subcutaneous, intra-arterial, intrasynovial, and intrarectal.

Other aspects of the invention provide methods for the treatment of infection by a human immunodeficiency virus (HIV) in a subject in need thereof comprising administering to a subject in need an effective amount of a composition comprising an inhibitor of one or more components of the SET complex. In some embodiments, the component of the SET complex being inhibited is selected from the group consisting of APE1, NM23-H1, TREX1, SET, HMGB2, and Pp32. In some embodiments of this aspect and all aspects described herein, the inhibitor of the SET complex is an antibody or antigen-binding fragment thereof, a small molecule, a peptide, or a nucleic acid. In some embodiments, the inhibitor is a nucleic acid that comprises a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:9.

Another aspect of the present invention relates to methods for the treatment of a retroviral infection in a subject in need thereof comprising administering to a subject in need an effective amount of a composition comprising an inhibitor of one or more base excision repair enzymes. In some embodiments, the base excision repair enzyme being inhibited is selected from the group consisting of OGG1, NTHL1, NEIL1, NEIL2, NEIL3, MUTYH, MPG, UNG, SMUG1, TDG, MBD4, APEX1, POLB, FEN1, XRCC1, and LIG3. In some embodiments, the inhibitor of the base excision repair enzyme is an antibody or antigen-binding fragment thereof, a small molecule, a peptide, or a nucleic acid. In some embodiments, the inhibitor is a nucleic acid comprising a sequence selected from the group consisting of SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14. In some embodiments, the retrovirus is a lentivirus. In some embodiments, the the lentivirus is a human immunodeficiency virus (HIV).

Other aspects of the invention provide methods for the treatment of infection by a human immunodeficiency virus (HIV) in a subject in need thereof comprising administering to a subject in need an effective amount of a composition comprising an inhibitor of one or more base excision repair enzymes. In some embodiments, the base excision repair enzyme being inhibited is selected from the group consisting of OGG1, NTHL1, NEIL1, NEIL2, NEIL3, MUTYH, MPG, UNG, SMUG1, TDG, MBD4, APEX1, POLB, FEN1, XRCC1, and LIG3. In some embodiments, the inhibitor of the base excision repair enzyme is an antibody or antigen-binding fragment thereof, a small molecule, a peptide, or a nucleic acid. In some embodiments, the inhibitor is a nucleic acid comprising a sequence selected from the group consisting of SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14.

Another aspect of the invention provides pharmaceutical compositions comprising an inhibitor of one or more components of the SET complex and a pharmaceutically acceptable carrier. In some embodiments, the component of the SET complex being inhibited is selected from selected from the group consisting of APE1, NM23-H1, TREX1, SET, HMGB2, and Pp32. In some embodiments of this aspect and all aspects described herein, the inhibitor of the SET complex is an antibody or antigen-binding fragment thereof, a small molecule, a peptide, or a nucleic acid. In some embodiments, the inhibitor is a nucleic acid that comprises the sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:9. In some embodiments of this aspect and all aspects described herein, the compositions further comprise one or more anti-HIV agents. In some embodiments, the anti-HIV agent is a nucleoside reverse transcriptase inhibitor, non-nucleoside reverse transcriptase inhibitor, integrase inhibitor, protease inhibitor, or any combination thereof. In some embodiments, the composition further comprises an inhibitor of one or more base excision repair enzymes and a pharmaceutically acceptable carrier. In some embodiments, the base excision repair enzymes being inhibited are selected from the group consisting of OGG1, NTHL1, NEIL1, NEIL2, NEIL3, MUTYH, MPG, UNG, SMUG1, TDG, MBD4, APEX1, POLB, FEN1, XRCC1, and LIG3.

Further aspects of the invention relate to the use of a composition comprising an inhibitor of one or more components of the SET complex and a pharmaceutically acceptable carrier as described herein. In one aspect, a composition comprising an inhibitor of one or more components of the SET complex and a pharmaceutically acceptable carrier can be used in a composition for therapeutic treatment of a subject with a retroviral infection, such as, but not limited to, HIV-1. Another aspect provides a use of a composition comprising an inhibitor of one or more components of the SET complex and a pharmaceutically acceptable carrier for the preparation of a medicament for the therapeutic treatment of a subject with a retroviral infection, such as, but not limited to, HIV-1.

In some embodiments, the component of the SET complex being inhibited is selected from the group consisting of APE1, NM23-H1, TREX1, SET, HMGB2, and Pp32. In some embodiments of this aspect and all aspects described herein, the inhibitor of the SET complex is an antibody or antigen-binding fragment thereof, a small molecule, a peptide, or a nucleic acid. In some embodiments, the inhibitor is a nucleic acid that comprises the sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:9. In some embodiments of this aspect and all aspects described herein, the compositions further comprise one or more anti-HIV agents. In some embodiments, the anti-HIV agent is a nucleoside reverse transcriptase inhibitor, non-nucleoside reverse transcriptase inhibitor, integrase inhibitor, protease inhibitor, or any combination thereof. In some embodiments, the composition further comprises an inhibitor of one or more base excision repair enzymes and a pharmaceutically acceptable carrier. In some embodiments, the base excision repair enzymes being inhibited are selected from the group consisting of OGG1, NTHL1, NEIL1, NEIL2, NEIL3, MUTYH, MPG, UNG, SMUG1, TDG, MBD4, APEX1, POLB, FEN1, XRCC1, and LIG3.

A further aspect of the invention provides pharmaceutical compositions comprising an inhibitor of one or more base excision repair enzymes and a pharmaceutically acceptable carrier. In some embodiments of this aspect and all aspects described herein, the base excision repair enzymes being inhibited are selected from the group consisting of OGG1, NTHL1, NEIL1, NEIL2, NEIL3, MUTYH, MPG, UNG, SMUG1, TDG, MBD4, APEX1, POLB, FEN1, XRCC1, and LIG3. In some embodiments, the inhibitor of the base excision repair enzyme is an antibody or antigen-binding fragment thereof, a small molecule, a peptide, or a nucleic acid. In some embodiments of this aspect and all aspects described herein, the inhibitor is a nucleic acid comprising a sequence selected from the group consisting of SEQ ID NO:7, SEQ ID NO:8, SEQ ID NO:9, SEQ ID NO:10, SEQ ID NO:11, SEQ ID NO:12, SEQ ID NO:13, SEQ ID NO:14, and SEQ ID NO:15. In some embodiments of this aspect and all aspects described herein, the compositions further comprise one or more anti-HIV agents. In some embodiments, the anti-HIV agent is a nucleoside reverse transcriptase inhibitor, non-nucleoside reverse transcriptase inhibitor, integrase inhibitor, protease inhibitor, or any combination thereof.

Other aspects of the invention relate to the use of a composition comprising an inhibitor of one or more base excision repair enzymes and a pharmaceutically acceptable carrier as described herein. In one aspect, a composition comprising an inhibitor of one or more components base excision repair enzymes and a pharmaceutically acceptable carrier can be used in a composition for therapeutic treatment of a subject with a retroviral infection, such as, but not limited to, HIV-1. Another aspect provides a use of a composition comprising an inhibitor of one or more components base excision repair enzymes and a pharmaceutically acceptable carrier for the preparation of a medicament for the therapeutic treatment of a subject with a retroviral infection, such as, but not limited to, HIV-1.

In some embodiments of this aspect and all aspects described herein, the base excision repair enzyme being inhibited is selected from the group consisting of OGG1, NTHL1, NEIL1, NEIL2, NEIL3, MUTYH, MPG, UNG, SMUG1, TDG, MBD4, APEX1, POLB, FEN1, XRCC1, and LIG3. In some embodiments, the inhibitor of the base excision repair enzyme is an antibody or antigen-binding fragment thereof, a small molecule, a peptide, or a nucleic acid. In some embodiments, the inhibitor is a nucleic acid comprising a sequence selected from the group consisting of SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14.

In some embodiments of this aspect and all aspects described herein, the compositions further comprise one or more anti-HIV agents. In some embodiments, the anti-HIV agent is a nucleoside reverse transcriptase inhibitor, non-nucleoside reverse transcriptase inhibitor, integrase inhibitor, protease inhibitor, or any combination thereof.

In other aspects, the invention provides methods for measuring retroviral DNA autointegration products in a cell. In one embodiment, the method comprises performing semi-quantitative PCR amplification of extrachromosomal DNA to generate first-round PCR products containing upstream or downstream long-terminal repeat sequences and internal viral DNA sequences, wherein the semiquantitative PCR amplification is performed using oligonucleotides that detect integration of a minus strand U3 CA-3' end into a retroviral DNA strand, and performing quantitative PCR amplification on said first-round PCR products to amplify fixed length long-terminal repeat sequences. In another embodiment, the method comprises the use of three DNA oligonucloetides designed to detect integration of a minus strand U3 CA-3' end into a retroviral DNA strand, wherein semiquantitative PCR amplification of extrachromosomal DNA generates first-round PCR products containing upstream or downstream long-terminal repeat sequences and internal viral DNA sequences followed by quantitative PCR analysis on said first-round PCR products to amplify fixed length long-terminal repeat sequences. In some embodiments, the methods further comprise the step of quantitative PCR analysis of mitochondrial DNA and extrachromosomal DNA fractions to measure stage-specific viral DNA products. In some embodiments, the methods further comprise the measurement of integrated retroviral DNA in chromosomal fractions.

BRIEF DESCRIPTION OF FIGURES

FIG. 1A shows knockdown and over-expression of SET complex proteins. SET-in is an siRNA-insensitive FLAG-tagged protein. Trex1 knockdown, assayed by qRT-PCR, reduced TREX1 mRNA by 94%. FIG. 1B demonstrates that SET and/or NM23-H1 knockdown inhibits HIV-$1_{IIIB}$ infection. HeLaCD4 cells transfected with a non-targeting control siRNA (CTL) or siRNAs targeting SET and/or NM23-H1 were infected with HIV-$1_{IIIB}$ and infection was assayed by p24 release. FIG. 1C shows that SET and/or NM23-H1 knockdown blocks single round HIV-Luc infection. HeLaCD4 cells were transfected with indicated siRNAs and infected with VSV-G pseudotyped HIV-Luc. Luciferase (Luc) activity, measured 48 hpi and normalized to total cellular protein, is compared to Luc activity in cells transfected with control siRNA. FIG. 1D demonstrates that expression of siRNA-insensitive SET (SET-in) rescues the HIV-Luc infection block caused by knocking down endogenous SET. 293T cells, transfected with control or SET siRNAs and then transfected two days later with empty vector or SET-in and pCMV-β-gal plasmids, were infected with HIV-Luc 24 h after transfection and Luc activity measured 48 h later was normalized to β-galactosidase activity. FIG. 1E shows that expression from transfected HIV-Luc DNA is not affected by SET/NM23-H1 knockdown. HeLaCD4 cells were transfected with HIV-Luc plasmid two days following siRNA transfection. Luc activity was measured 24 h later and normalized as shown in FIG. 1D. FIG. 1F depicts that knockdown of other SET complex proteins also inhibits HIV-Luc, but not MLV or ASV single-round reporter viruses, with the exception of pp32, which also inhibits the simple retroviruses. Luc activity was measured 48 hpi. The role of pp32 in simple retroviral infection could be due to SET-complex independent effects. FIG. 1G demonstrates that SET/NM23-H1 knockdown inhibits SIV-Luc infection. *p<0.001 relative to control knockdown in panels of FIGS. 1B, 1C, 1G and 1F. Mean and standard deviation (S.D.) from at least four independent infections are shown in FIGS. 1B-1G. FIG. 1H shows that virions released by control and SET/NM23-H1 knockdown cells are equally infectious. Viral supernatants from control and SET/NM23-H1 knockdown HeLaCD4 cells (24 h post HIVIIIB infection) were normalized by p24 content and an equal amount of virons was applied to TZM-b1 cells, which are stably transfected with an LTR-driven Luc reporter gene. Luc activity was measured 48 hpi. FIG. 1I shows that the infection block caused by SET/NM23-H1 knockdown also affects HIV-Luc viruses packaged with HIV Env. HIV-Luc viruses packaged with HIV Env were used to infect control or SET/NM23-H1 or CD4 knockdown cells. Luc activity was measured 48 hpi.

FIGS. 2A-2C show late RT products (normalized to mitochondrial DNA) (FIG. 2A) and integrated DNA (normalized to β-globin gene) (FIG. 2B), measured at indicated times, and 2-LTR circles, measured 24 hpi (FIG. 2C), which were quantified by qPCR from control (black) or SET/NM23-H1 (gray) knockdown cells. Data are mean+/−S.D. of triplicate measurements from 3 independent experiments, normalized to control knockdown cells. *, $p<0.001$. FIG. 2D shows that SET/NM23-H1 knockdown does not affect chromosomal integration site preferences, but enhances autointegration. DNA was cloned and sequenced from the Hirt pellet. FIG. 2E depicts the sites of autointegration. Each site within 2 regions of the HIV-1 genome, numbered based on the HIV-1$_{NL4-3}$ strain, is represented as a dot. Autointegrants in control siRNA treated cells are black and SET plus NM23-H1 knockdown cells are lighter. FIG. 2F demonstrates that the consensus sequence for autointegration is indistinguishable between control and SET/NM23-H1 knockdown cells. Nucleotide frequency at each position is shown as the percent of expected frequency if autointegration were random. Frequencies <70% (dark) or >130% (light) of expected (corresponding to $p<0.001$) are in bold. The position 0 nucleotide is joined to the processed U3 end of the LTR. Nucleotide sequences for positions 0-14 were experimentally determined by sequencing; those for positions −10 to −1 were assumed from the HIV-Luc sequence upstream of the mapped integration sites.

FIG. 3A depicts a schematic of HIV-1 auto-PCR nested PCR assay. The common primer binding site (PBS-) (reverse) primer is used to amplify same strand integrants with the A+ (forward) primer or opposite strand integrants with the B− (reverse) primer during first-round PCR. A single length nested PCR product is then amplified using an LTR primer pair (R-U5) during second-round qPCR. Filled circles, internal viral 5' phosphates attacked during autointegration. FIG. 3B depicts the kinetics of stage-specific HIV-1 DNA product formation. Late RT, autointegrants, and 2-LTR circles were normalized to mitochondrial DNA; integrated DNA was normalized to β-globin. Values of late RT and autointegration are shown relative to peak values 10 hpi, while 2-LTR and integrated DNA are normalized to peak 24 hpi values. Mean and S.D. from triplicate qPCR measurements are shown. FIGS. 3C-3E demonstrate that active IN is required for autointegration. HeLaCD4 cells were infected with HIV-Luc carrying wild type (WT) or mutant (mt) IN. Luc activity was measured 48 hpi (FIG. 3C) and auto-PCR was performed 10 hpi (FIG. 3D). First-round PCR products (FIG. 3E) from the Hirt supernatant DNA were analyzed by agarose gel electrophoresis. FIG. 3F shows stage specific HIV-1 DNAs from control and SET/NM23-H1 knockdown cells infected with HIV-Luc. Late RT (LRT) and autointegration were measured 10 hpi and chromosomal integration was assayed 24 hpi. Mean and S.D. from triplicate qPCR assays of three independent experiments are shown. *, $p<0.01$. FIG. 3G demonstrates that autointegration is not an obligate by-product of failed integration. Autointegration was measured 10 hpi and Luc activity at 48 hpi. The difference in autointegration is not significant. FIG. 3H shows that knocking down SET complex proteins TREX1 or APE1 also increases autointegration. Mean plus S.D. from two independent experiments are shown. *, $p<0.01$. FIG. 3I demonstrates that NM23-H1 over-expression suppresses autointegration. MDA-MB-435, an NM23-H1 deficient metastatic breast cancer cell line, stably transfected with vector (C-100) or an NM23-H1 expression plasmid (H1-117), was infected with VSV-G pseudotyped HIV-Luc, and LRT and autointegrants were measured 10 hpi. *$p<0.01$. FIG. 3J shows that SET and NM23-H1 associate with HIV-1 cDNA. Cytoplasmic extracts from infected HeLaCD4 cells were immunoprecipitated with the indicated antibodies (mouse (m) or rabbit (rab)) and associated HIV-1 cDNA was quantified by qPCR. Mean plus S.D. from 3 independent experiments are shown. FIG. 3K depicts a detailed diagram of auto-PCR assay. Primers PBS-/A+ and PBS-/B− amplify same-strand and opposite-strand joining products, respectively, during first-round PCR. The resulting products contain PBS-LTR (U3RU5) sequences, which are measured by second-round nested qPCR using R-U5 primers. Arrowheads, reverse transcript 5' ends; filled circles, 5' phosphates attacked by the recessed CA-OH ends during autointegration. The viral DNA ends become joined to these internal sites during CA-OH attack; the structures in brackets are imaginary intermediates to aid visualization of reaction pathways. Open circles, internal 3' termini resulting from autointegration. FIG. 3L-3N shows that knocking down BAF does not affect HIV autointegration. FIG. 3L is an immunoblot demonstrating knockdown of BAF protein by BAF siRNA but not control siRNA (CTL) or BAF-C siRNA (which contains three mismatches compared to BAF siRNA (M. C. Shun, J Virol 81, 166 (2007)). By densitometry only 8% of BAF protein remained at the time cells were infected with HIV-Luc 48 h after transfection. BAF knockdown inhibited HIV infection about 2-fold as measured by Luc activity (FIG. 3M), but had no effect on autointegration (FIG. 3N). Infectivity and autointegration were measured as before. Mean and S.D. of two independent experiments are shown. FIG. 3O shows that the majority of autointegration products are detected in the cytoplasm. Infected HeLaCD4 cells were fractionated into cytoplasmic and nuclear fractions 10 hpi, and extrachromosomal DNA was extracted from each fraction using the Hirt method and analyzed by the auto-PCR assay. Mean percentage (and S.D.) of total autointegrants in each fraction is shown. The immunoblot was probed for C23 (nuclear marker) and tubulin (cytoplasm marker) to demonstrate the efficiency of cytoplasmic versus nuclear fractionation.

FIGS. 4A-4C depict how increasing dU incorporation into HIV-1 reverse transcripts decreases autointegration and increases infection. HeLaCD4 cells were cultured overnight in media supplemented with increasing amounts of dUTP (FIG. 4A, FIG. 4C) or BrdU (FIG. 4B) and then infected with HIV-Luc. Autointegration was measured 10 hpi and normalized to either mitochondrial DNA (black) or late RT (gray) and Luc activity was measured 48 hpi. Mean plus S.D. for triplicate assays of 3 experiments are normalized to cultures containing no added uracil. *, $p<0.01$. FIGS. 4D-4F demonstrate that increasing virion-associated APOBEG3G (A3G) decreases autointegration. Late RT product (FIG. 4D) or autointegrants (FIG. 4E, (FIG. 4F) were amplified 10 hpi with HIV-Luc/ΔVif viruses, generated in 293T cells cotransfected with indicated amounts of A3G plasmid. Both LRT and autointegration were inhibited by increasing viral cytidine deamination, but autointegration decreased to a greater extent. In FIG. 4E auto-PCR products were normalized to either mitochondrial DNA (black) or LRT (gray). *, $p<0.001$. In FIG. 4F cells were transfected with siRNAs targeting indicated SET complex components and then infected with ΔVif virus generated in cells transfected with no A3G or 100 ng A3G plasmid. Autointegrants were analyzed 10 hpi and normalized relative to mitochondrial DNA and results with virus lacking packaged A3G. FIG. 4G demonstrates that knocking down upstream and downstream BER genes, UNG2 and POLB, also increases autointegration. Stage specific HIV-1 DNA was measured as shown in FIG. 3F. *, p<0.01. FIG. 4H measures autointegration in polb knockout cells. polb$^{+/+}$ and polb$^{-/-}$ MEF were infected with HIV-Luc (WT) or HIV-Luc/ΔVif/A3G (100 ng) virus and autointegration was measured as above and normalized relative to either mitochondrial DNA (black) or LRT (gray). Autointegration is enhanced in polb$^{-/-}$MEF and further increased by increasing cytidine deaminase activity in virions. *, p<0.01. FIGS. 4I-4K show that late RT levels are affected by high dose BrdU treatment and in polb−/− MEF. HeLaCD4 cells were grown in media containing the indicated concentration of dUTP (FIG. 4I) or BrdU (FIG. 4J) overnight and infected the next morning. Late RT products were assayed 10 hpi. (FIG. 4K) polb+/+ and polb−/− cells were similarly infected and analyzed for late RT levels. *, p<0.01. FIG. 4L demonstrates that knockdown of SET components blocks ΔVif and ΔVif/A3G infection as well as HIV-Luc infection. HeLaCD4 cells, transfected two days earlier with the indicated siRNAs, were infected with HIV-Luc (WT), HIV-Luc/ΔVif, or HIV-Luc/ΔVif/A3G (produced in cells transfected with 100 ng A3G plasmid). Infection was measured by Luc activity 48 hpi.

DETAILED DESCRIPTION

Figure 1:
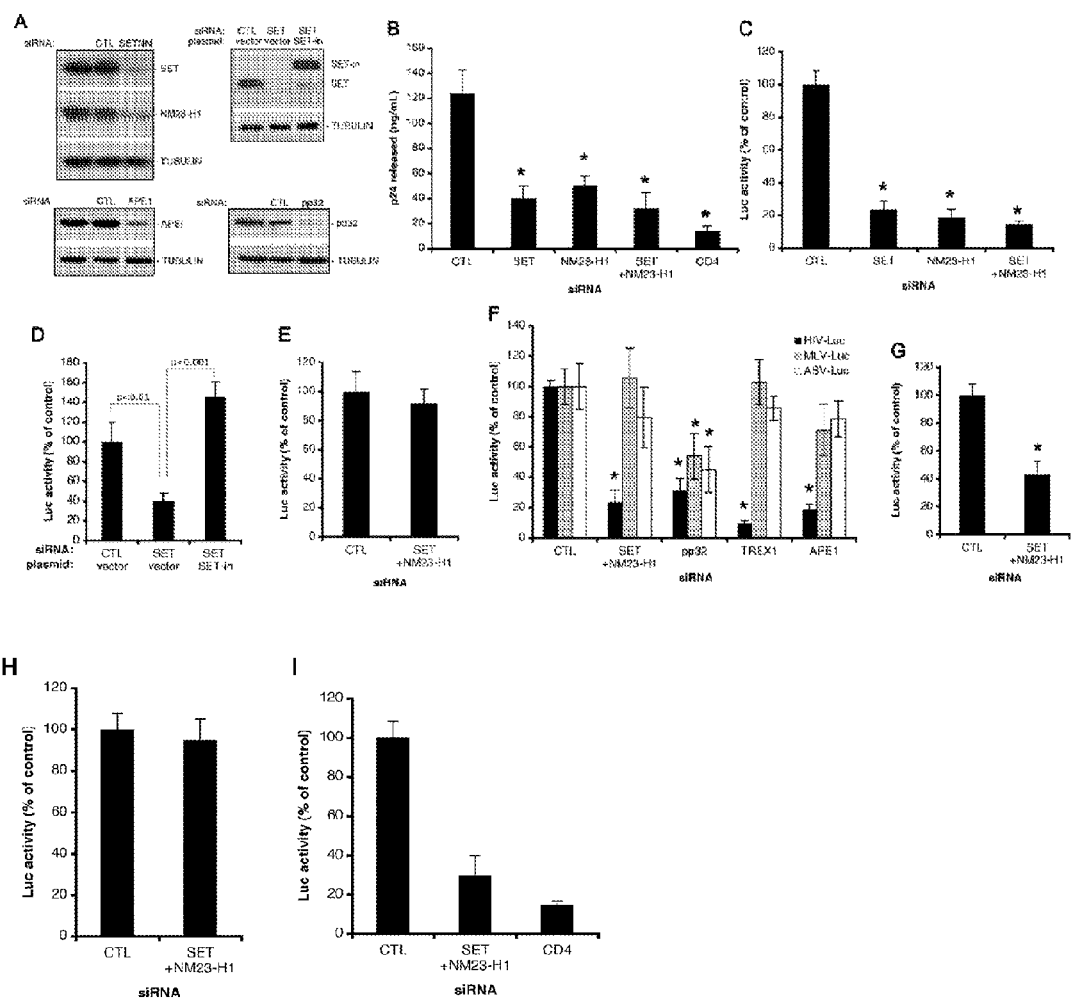
FIG. 1 demonstrates that the SET complex facilitates HIV-1 infection.

3'-processing of retroviral dsDNA can occur soon after the DNA ends are synthesized by reverse transcription in the cytoplasm (M. D. Miller et al., J Virol 71, 5382 (1997)). Host cytosolic DNA-interacting proteins were therefore considered as potential regulators of autointegration. One candidate is the SET complex, an endoplasmic reticulum (ER)-associated DNA repair complex that contains three DNases and is mobilized to the nucleus in response to oxidative stress. The SET complex was originally discovered as a Granzyme A (GzmA) target in cells undergoing caspase-independent T cell-mediated death (P. J. Beresford et al., J Biol Chem 276, 43285 (2001)). Two nucleases in the complex, the endonuclease NM23-H1 and the exonuclease TREX1, are activated by GzmA cleavage of the inhibitor SET protein to cause single-stranded DNA damage (D. Chowdhury et al., Mol Cell 23, 133 (2006); Z. Fan et al., Cell 112, 659 (2003)). In addition to the three DNases (APE1, NM23-H1, TREX1) and SET (a histone chaperone of the nucleosome assembly protein family), the SET complex contains HMGB2, a DNA binding protein that preferentially binds to distorted or damaged DNA, and the PP2A inhibitor pp32 (Z. Fan et al., Mol Cell Biol 22, 2810 (2002)). Although individual SET complex components have been implicated in diverse processes (including DNA repair, histone modification, DNA replication, transcriptional activation, single-stranded DNA degradation, autoimmunity), the functions of the intact complex are not well understood (D. Chowdhury and J. Lieberman, Annu Rev Immunol 26, 389 (2008)).

The methods and compositions described herein are useful for treating or preventing a retroviral infection. Aspects of the present invention relate to compositions comprising an inhibitor of one or more components of the SET complex, and methods of use of such compositions in the treatment of cells infected with a retrovirus to prevent integration of viral nucleic into host nucleic acids, and thus prevent or inhibit further viral propagation and/or replication.

Retroviruses and Retroviral Integration

The methods and compositions of the invention are useful for the inhibition and/or prevention of retroviral propogation and/or replication. Retroviruses are maintained as proviral DNAs that are integrated into the genome of somatic cells. Mammalian cells have evolved mechanisms to limit or restrict retroviral replication, constituting novel aspects of intrinsic immunity. Retroviruses, in turn, have evolved mechanisms to inactivate or overcome such blocks to infection (D. Wolf and S. P. Goff, 2008, Ann. Rev. Gen., 42: 143-163).

Integration into the genome of the host cell is a defining feature of retroviral replication. Once integrated, the retroviral DNA is replicated along with cellular DNA during each cycle of cell division. The retroviral DNA is synthesized by reverse transcription of the retroviral RNA genome that enters the host cell upon infection. Reverse transcription takes place in the reverse transcription complex (RTC), a nucleoprotein complex that is derived from the core of the infecting virion. The synthesis of full-length retroviral DNA in the RTC produces a large nucleoprotein complex termed the pre-integration complex (PIC). The newly synthesized retroviral DNA remains associated with viral and cellular proteins the (PIC). The viral integrase protein that integrates retroviral DNA into the host genome is one of the key components of the PIC. As reverse transcription occurs in the cytoplasm, the PIC must be transported to the nuclear periphery and cross the nuclear envelope before integration of the viral DNA into the host chromosome. (Y. Suzuki and R. Craigie, 2007, Nat Rev Microbiol, 5:187-196). Once the retroviral nucleoprotein complex reaches the nucleus it must cross the nuclear envelope to integrate into the chromosomal DNA.

Any retrovirus, as described herein, can be a target of the methods and compositions of the present invention. Thus, a "retrovirus", as described herein, refers to any enveloped RNA virus, belonging to the viral family Retroviridae, that replicates in a host cell via the enzyme reverse transcriptase to produce DNA from its RNA genome. The retroviral DNA is then incorporated into the host's genome by an integrase enzyme. The retrovirus thereafter replicates as part of the host cell's DNA. The retrovirus itself stores its nucleic acid, in the form of a +mRNA (including the 5'cap and 3'PolyA inside the virion) genome and serves as a means of delivery of that genome into cells it targets as an obligate parasite, and constitutes the infection. As used herein, a "provirus" refers to retroviral DNA once it is integrated into the genome of a host cell. Retrovirus genomes commonly include, but are not limited to, three open reading frames that encode for proteins that can be found in the mature virus: group-specific antigen (gag) encoding for core and structural proteins of the virus; polymerase (pol) coding for reverse transcriptase, protease and integrase; and envelope (env) coding for the retroviral coat proteins.

The genera belonging to the family of Retroviridae include, but are not limited to:

Alpharetrovirus: Members of "Alpharetrovirus" have a type C morphology, and can cause sarcomas, other tumors, and anaemia of wild and domestic birds and also affect rats. Alpharetrovirus species include, but are not limited to, the Rous sarcoma virus, avian leukosis virus, and avian myeloblastosis virus. Rous sarcoma virus, Avian carcinoma Mill Hill virus 2, Avian myelocytomatosis virus 29, Avian sarcoma virus CT10, Fujinami sarcoma virus, UR2 sarcoma virus, and the Y73 sarcoma virus.

Betaretrovirus: Members of "Betaretrovirus" have a type B or type C morphology. The type B is common for a few exogenous, vertically transmitted and endogenous viruses of mice, while some primate and sheep viruses are type D. Betaretrovirus species include, but are not limited to, Jaagsiekte sheep retrovirus, Langur virus, Mason-Pfizer monkey virus, Squirrel monkey retrovirus, and mouse mammary tumour virus.

Gammaretrovirus: Members of "Gammaretrovirus" often contain oncogenes and cause sarcomas and leukemias. Gammaretrovirus species include, but are not limited to the murine leukemia virus, the feline leukemia virus, the feline sarcoma virus, Gibbon ape leukemia virus, Guinea pig type-C oncovirus, Porcine type-C oncovirus, Finkel-Biskis-Jinkins murine sarcoma virus, Gardner-Arnstein feline sarcoma virus, Hardy-Zuckerman feline sarcoma virus, Harvey murine sarcoma virus, Kirsten murine sarcoma virus, Moloney murine sarcoma virus, Snyder-Theilen feline sarcoma virus, Woolly monkey sarcoma virus, and the avian reticuloendotheliosis viruses, including, but not limited to, Chick syncytial virus, Reticuloendotheliosis virus, and Trager duck spleen necrosis virus. Many endogenous retroviruses, closely related to exogenous gammaretroviruses are present in the DNA of mammals (including humans), birds, reptiles and amphibians.

Deltaretrovirus: The "Deltaretrovirus" genus consists of exogenous horizontally-transmitted viruses found in several groups of mammals. Examples include, but are not limited to, the bovine leukemia virus and the Human T-lymphotropic virus.

Lentiviruses: "Lentiviruses", as defined herein, are a genus of retroviruses that includes bovine lentiviruses (e.g., bovine immunodeficiency virus, Jembrana disease virus), equine lentiviruses (e.g. equine infectious anemia virus), feline lentiviruses (e.g. feline immunodeficiency virus), ovine/caprine lentivirus (e.g. caprine arthritis-encephalitis virus, ovine lentivirus, visna virus) and primate lentivirus group. The primate lentivirus group includes human immunodeficiency virus (HIV), including human immunodeficiency virus type 1 (HIV-1), human immunodeficiency virus type 2 (HIV-2), and human immunodeficiency virus type 3 (HIV-3), as well as simian AIDS retrovirus SRV-1, including human T-cell lymphotropic virus type 4 (HIV-4) and simian immunodeficiency virus (SIV). The env genes of HIV-1, HIV-2 and SIV all produce an envelope glycoprotein, which is cleaved, with one portion being an exterior viral envelope protein subunit referred to as gp120. The binding and fusion of HIV-1, HIV-2 and SIV viruses with cells is mediated by specific interaction between the external subunit of this gp120 viral envelope protein and the CD4 receptor on the target cell surface (Dalgleish, et al., Nature, 312:763-767 (1984); Klatzmann, et al., Nature, 312:767-768 (1984); Berger, et al., PNAS, 85:2357-2361 (1988)).

Retroviral Autointegration and the SET Complex

Relatively little is known about the host proteins that associate with the PIC and assist in retroviral, e.g., HIV-1, nucleic acid integration into a host cell genome. The core of an infecting retrovirus comprises a nucleoprotein complex in which the viral RNA genome is associated with enzymes and structural proteins that are required for reverse transcription and subsequent integration of the viral genome into host DNA. After reverse transcription, the viral DNA and at least the viral integrase protein must remain associated within the nucleoprotein complex until the integration reaction inserts the viral DNA into a chromosome of the host cell.

The process of "retroviral DNA integration", "retroviral nucleic acid integration" or "provirus formation", as defined herein, comprises: (1) 3' processing (integrase (IN)-mediated hydrolysis of GT dinucleotides from each 3' end of the initially blunt-ended retroviral DNA to produce reactive, recessed $CA_{OH}$-3' ends); (2) DNA strand transfer (IN-mediated insertion of the cleaved 3' ends of the viral DNA into the 5' ends of the opposing strands of host chromosomal DNA); and (3) 5'-end joining (repair by host enzymes of the gaps between the 5'-ends of viral DNA and the chromosome). Any of these steps are useful as targets for the methods and compositions of the present invention.

While the 3' processing of the retroviral DNA is required for host integration, 3'-processing also makes the retroviral DNA vulnerable to "autointegration" in which the reactive CA ends attack sites within the retroviral DNA itself. "Autointegration", as defined herein, is mechanistically analogous to chromosomal integration, but results in nonproductive deletion or inversion circles of the retroviral DNA through intramolecular integration of the retroviral DNA. A striking feature of the reactions with INCs isolated from cells infected with retroviruses, for example, MoMLV and HIV-1, is the strong preference to integrate intermolecularly into another DNA molecule, rather than undergo autointegration.

As defined herein, the term "retroviral infection" or "infection by a retrovirus" refers to any condition wherein a virus has entered a host cell, and wherein the nucleic acid of said retrovirus, had, has, or will be undergoing integration into a host nucleic acid to mediate provirus formation and retroviral infection. Thus, as used herein, a "productive retroviral infection" refers to a retroviral infection wherein a nucleic acid of the retrovirus has successfully integrated into a host nucleic acid and provirus formation has occurred. Thus, as described herein, a "retroviral infection" includes both non-productive (no provirus formation or incomplete retroviral integration) and productive retroviral infections (retroviral integration and provirus formation). The retrovirus may be any retrovirus as described herein, and in some embodiments, the retrovirus is HIV.

The inventors have surprisingly discovered that retroviruses, such as HIV-1, subvert components of the host SET complex to prevent autointegration of retroviral nucleic acid during the process of retroviral DNA integration and provirus formation. Thus, some aspects of the present invention relate to methods and compositions for promoting autointegration of retroviral nucleic acid and the inhibition of retroviral DNA integration in a cell, by targeting one or more components or activities of the SET complex. The cell may be a dividing or a non-dividing cell, depending on the nature of the retroviral infection. For example, retroviruses such as MoMLV require cell division to replicate and wait for the nuclear envelope to break down during mitosis. In contrast to MoMLV, HIV-1 and other lentiviruses can infect both dividing and non-dividing cells. For example, HIV-1 can replicate in certain quiescent or terminally differentiated cells, including macrophages and microglia, in which the cell cycle is stopped at the G0 phase. The ability to infect non-dividing cells is not restricted to lentiviruses. Avian sarcoma virus (ASV), as well as Friend murine leukaemia virus (FrMLV), can infect non-dividing cells including growth-arrested cells, neurons and macrophages, albeit less efficiently than HIV-1. Cell-cycle-independent infection has been also proposed for other retroviruses, including HFV and spleen necrosis virus.

The "SET complex", as defined herein, refers to a 270-420 kDa endoplasmic reticulum-associated DNA repair complex that is mobilized to the nucleus in response to oxidative stress. The SET complex was originally discovered as a Granzyme A (GzmA) target in cells undergoing caspase-independent T cell-mediated death. The SET complex is known to comprise three DNA nucleases (APE1, NM23-H1, TREX1), a NAP family histone chaperone (SET), a DNA binding protein (HMGB2), and a PP2A phophatase inhibitor (pp32).

Accordingly, one aspect of the invention provides a method for increasing autointegration of retroviral nucleic acid comprising contacting a cell infected with a retrovirus with an inhibitor of a component or activity of the SET complex. In some embodiments, a component of the SET complex is selected from the group consisting of APE1, NM23-H1, TREX1, SET, HMGB2, and Pp32. One or more components of the SET complex may be targeted according to the methods of the present invention. Other related aspects of the invention provide a method for increasing autointegration of retroviral nucleic acid comprising contacting a cell infected with a retrovirus with an inhibitor of a base excision repair enzyme. In some embodiments, the base excision repair enzyme is selected from the group consisting of OGG1, NTHL1, NEIL1, NEIL2, NEIL3, MUTYH, MPG, UNG, SMUG1, TDG, MBD4, APEX1, POLB, FEN1, XRCC1, and LIG3.

Another aspect of the present invention relates to methods of preventing retroviral nucleic acid integration into a target nucleic acid or host cell. In one embodiment of this aspect and all other aspects described herein, the method comprises contacting a cell infected with a retrovirus with an inhibitor of a component or activity of the SET complex. In some embodiments, a component of the SET complex is selected from the group consisting of APE1, NM23-H1, TREX1, SET, HMGB2, and Pp32. One or more components or activities of the SET complex may be targeted according to the methods of the present invention. Other related aspects of the invention provide a method for increasing autointegration of retroviral nucleic acid comprising contacting a cell infected with a retrovirus with an inhibitor of a base excision repair enzyme. In some embodiments, the base excision repair enzyme is selected from the group consisting of OGG1, NTHL1, NEIL1, NEIL2, NEIL3, MUTYH, MPG, UNG, SMUG1, TDG, MBD4, APEX1, POLB, FEN1, XRCC1, and LIG3.

A further aspect of the present invention relates to methods of inhibiting proviral formation in a cell. In one embodiment of this aspect and all other aspects described herein, the method comprises contacting a cell infected with a retrovirus with an inhibitor of a component or activity of the SET complex. In some embodiments, a component of the SET complex is selected from the group consisting of APE1, NM23-H1, TREX1, SET, HMGB2, and Pp32. One or more components of the SET complex may be targeted according to the methods of the present invention. Other related aspects of the invention provide a method for increasing autointegration of retroviral nucleic acid comprising contacting a cell infected with a retrovirus with an inhibitor of a base excision repair enzyme. In some embodiments, the base excision repair enzyme is selected from the group consisting of OGG1, NTHL1, NEIL1, NEIL2, NEIL3, MUTYH, MPG, UNG, SMUG1, TDG, MBD4, APEX1, POLB, FEN1, XRCC1, and LIG3.

In some embodiments of these aspects and all other aspects described herein, one or more components or activities of the SET complex are inhibited using the methods and compositions of the present invention. Components of the SET complex include, but are not limited to, the DNA nucleases (APE1, NM23-H1, TREX1), a NAP family histone chaperone (SET), a DNA binding protein (HMGB2), and a PP2A phophatase inhibitor. While the SET complex and its component factors likely have a number of activities, as used herein a "SET complex activity" or "activity of the SET complex" refers to the role the SET complex plays in preventing retroviral autointegration. Thus, an "inhibitor" of the SET complex, or its activity thereof, will interfere with the prevention or inhibition by the SET complex of retroviral autointegration. The same is true of a component of the SET complex as described herein. That is, despite other potential or demonstrated roles for the various components, the "activity" of the component protein refers to its participation in the suppression of retroviral autointegration. An "inhibitor" of any such component, i.e., APE1, NM23-H1, TREX1, SET, HMGB2, or Pp32, will necessarily inhibit at least this activity of the component of the SET complex. Such inhibition can be measured using any assay available to one of ordinary skill in the art. In some embodiments, the inhibition is measured using the autointegration assays used herein. Any sequence or domain of one or any combination of these components of the SET complex involved in mediating SET complex activity is a useful target for the SET complex inhibitors used in the methods and compositions of the present invention. Similarly, the mRNA for each of these components of the SET complex can also be targeted for degradation, e.g., by antisense or siRNA method as described herein.

As used herein, "SET protein", "SET", "PHAPII", "TAF-Iβ (template activating factor 1b)" "INHAT", "IGAAD", "StF-IT-1", or "$I_2^{PP2A}$", Entrez GeneID: 6418, refers to the component of the SET complex that is a nucleosome assembly protein (NAP) known to inhibit DNA methylation and histone acetylation (For the avoidance of doubt, "SET activity" refers herein to the role SET plays in preventing autointegration of the retroviral DNA. Thus, an inhibitor of SET activity will interfere with the role of SET in the prevention of autointegration. TAF-I exists in two isoforms, TAF-Iα and SET/TAF-Iβ, which are generated by alternative splicing. The two isoforms are identical except for a short N-terminal sequence (1-37 amino acids of TAF-Iα and 1-24 amino acids of SET/TAF-Iβ). SET is highly conserved in frog, mouse, rat, and human. SET homologues are also found in invertebrates. Spr-2, which has approximately 38% sequence identity to human SET, has been identified in *C. elegans*. *Saccharomyces cerevisiae* Vps75, recently identified as a NAP1 family protein, is similar to TAF-I in its domain structure and in its preference for binding histones H3-H4. TAF-I has nucleosome assembly activity. SET also exhibits sperm chromatin decondensation activity, similar to NAP1, and is thus functionally related to NAP1. The crystal structure of SET-DC (1-225 amino acids), which is composed of the N-terminal helix, the backbone helix, and the earmuff domain, forms a dimer that assumes a headphone-like structure similar to that of NAP1. The structure-function relationships of SET have been intensively studied on the basis of the crystal structure. Interaction between SET and histones has been confirmed in vivo and in vitro. SET preferentially binds to histones H3 and H4, although all core histones can bind to SET, and full-length SET binds to all four core histones, whereas a SET DC deletion protein, which lacks the C-terminal acidic stretch, only binds histones H3 and H4 in vitro. A biochemical study with SET mutants showed that the lower part of the earmuff domain is used for binding both core histones and dsDNA. In addition, mutants with impaired histone and DNA binding activities have weak histone chaperone activity. SET specifically binds to unacetylated, hypoacetylated, and repressively marked histones but not to hyperacetylated histones. SET can also be isolated as a subunit of the INHAT complex, a multiprotein complex that potently inhibits the histone acetyltransferase activities of p300/CBP and PCAF. SET can also be isolated by affinity purification of factors interacting with the DNA-binding domain of the transcription factors KLF5 and Sp1. SET inhibits the DNA binding activities of both KLF5 and Sp1 and interferes with their transactivation activities. In addition, SET can interact with nuclear receptor-type transcription factors such as estrogen receptor a (ERa), progesterone receptor B, thyroid receptor b, and RXR a. Other examples of the involvement of SET in promoter specific transcriptional regulation have been reported, including: regulating transcription along with other transcription factors such as COUP-TF (chicken ovalbumin upstream promoter transcription factor), NGF-IB (nerve growth factor inducible protein B), and SF-1 (steroidogenic factor-1) to regulate P450c17 genespecific transcription; and regulating the KAI1 gene-promoter-specific transcription by binding to the adaptor protein Fe65. SET also has roles in phenomena such as gene translocation; caspase-independent apoptosis, which depends on its digestion by the trypsin-like protease GzmA; cell-cycle regulation, which depends on its interaction with the CDK inhibitor; and cancer regulation, which depends on binding to leukemia-related factor (M. Eitoku, Cell. Mol. Life Sci. 65 (2008) 414-444).

As defined herein, "HMGB2" or "HMG2" (Entrez GeneID: 3148) refers to the component of the SET complex that is a member of the non-histone chromosomal high mobility group (HMG) protein family. The proteins of this family are chromatin-associated and ubiquitously distributed in the nucleus of higher eukaryotic cells. Studies have demonstrated that HMGB2 is able to efficiently bend DNA and form DNA circles, indicating a role in facilitating cooperative interactions between cis-acting proteins by promoting DNA flexibility. Functionally, HMGB2 participates in various pathways, including, but not limited to, apoptotic DNA fragmentation and tissue homeostasis, Granzyme A mediated Apoptosis Pathway, base-excision repair, DNA ligation, DNA repair, DNA replication, DNA unwinding during replication, establishment and/or maintenance of chromatin architecture, nucleosome assembly, phosphoinositide-mediated signaling, regulation of transcription from RNA polymerase II promoter and 1 other), and the DNA end-joining processes of DNA double-strand breaks repair and V(D)J recombination. HMGB2 has molecular functions (DNA bending activity, double-stranded DNA binding, single-stranded DNA binding, transcription factor activity) and localizes in various compartments (condensed chromosome, cytoplasm, nuclear chromosome, nucleus, perinuclear region of cytoplasm, chromatin). Protein that interact with HMGB2 include, but are not limited to, APEX1, CSNK1A1, GZMA, PGR, POU2F1, POU2F2, POU3F1, POU5F1, PRKDC, RAG1, SET, and TP53. The HMGB2 gene contains 8 different introns (5 gt-ag, 3 gc-ag). Transcription of HMGB2 produces 10 alternatively spliced mRNAs. There are 2 non overlapping alternative last exons and 8 validated alternative polyadenylation sites. The mRNAs differ by truncation of the 3' end, overlapping exons with different boundaries, alternative splicing or retention of 8 introns. The 9 spliced mRNAs putatively encode HMGB2 proteins, altogether 6 different isoforms (3 complete, 2 COOH complete, 1 partial), some containing HMG1/2 (high mobility group) box domain [Pfam], a coiled coil stretch [Psort2]. HMGB2 isoform(s) comprised by the SET complex as described herein are also targets for the inhibition of the activity of the SET complex.

"Pp32", "Anp32a", "Cl5orfl", "I1PP2A", "LANP", "Lanp 3", "MAPM", "MGC119787", "MGC150373", "Mapmodulin", or "PHAP1" (Entrez GeneID: 8125), as used herein, refers to the component of the SET complex that belongs to a family of evolutionarily conserved proteins known as the acidic nuclear phosphoprotein family (Anp32a-h). Members of the family help modulate cellular signaling and gene expression to regulate the morphology and dynamics of the cytoskeleton, cell adhesion, neuronal development, or cerebellar morphogenesis. Pp32 has been implicated in a number of cellular processes, including proliferation, differentiation, caspase-dependent and caspase-independent apoptosis, suppression of transformation (tumor suppressor), inhibition of protein phosphatase 2A, regulation of mRNA trafficking and stability inassociation with ELAVL1, inhibition of acetyltransferases as part of the INHAT (inhibitor of histone acetyltransferases) complex, and a role in E4F1-mediated transcriptional repression. Pp32 is expressed in normal tissues as well as in many breast, pancreas, and prostate cancers, where it can act as a tumor suppressor. Pp32 has also been associated with the neurodegenerative disease spinocerebellar ataxias through binding the polyglutamine repeats of Ataxin-1. The pp32 protein contains a nuclear localization signal (NLS, import signal) at the C terminus but can also bind the nuclear export protein Crm1 through the N terminus LRR domain, which allows pp32 to exist as a component of both nuclear and cytoplasmic complexes. Nuclear pp32 is found associated with the protein SET (TAF-Iβ in the INHAT (INHibitor of Acetyl Transferase Activity) complex, which regulates histone modification/transcription. Also, the SET complex contains pp32 as one of its components. pp32 can promote apoptosis by accelerating caspase-9 activation after apoptosome formation. Both pp32 and SET were initially isolated as potent inhibitors of protein phosphatase 2A (Li and Damuni, 1998), a cell cycle regulatory phosphatase. Pp32 also helps regulate cell cycle progression by associating with the hyperphosphorylated form of the retinoblastoma tumor suppressor. Pp32 is also involved in the regulation of mRNA trafficking through an association with Crm1 as part of the HuR complex. Since this complex transports the mRNAs of cytokines and proto-oncogenes, it can stabilize factors involved in tumor progression and cell differentiation, such as IL-6 and vascular endothelial growth factor. A structural role in cytoskeletal dynamics has also been inferred because the phosphorylated form of pp32 stimulates the localization of the Golgi apparatus in a microtubule and dynein-dependent manner via binding to the microtubule-associated proteins, MAP1, MAP2, and MAP4. The pp32 family (Anp32a-h) belongs to the superfamily of proteins containing leucine-rich repeats (LRRs). The LRR is a short motif of 20-29 residues in length that is present in tandem arrays in a variety of cytoplasmic, membrane, and extracellular proteins. The 28-kDa pp32 protein contains three capped LRR motifs at the N terminus and a highly acidic C terminus containing ~70% aspartic and glutamic acid residues. Similar acidic stretches are found in the nucleosome assembly proteins, nucleomorphin, nucleoplasmin, p62, and SET, and in the HMG box proteins, where the acidic domain is likely to be involved in chromatin binding. Acidic stretches are also found in proteins such as tubulin, which are responsible for microtubule association. The LRR domain is of particular importance, as it is the minimal fragment of pp32 necessary to bind to a hyperphosphorylated form of the retinoblastoma protein (Rb). In cancers where p16 is inactivated, such as pancreatic cancer, the cyclin D:CD4/6 complex is unregulated and hyperphosphorylated Rb is predominant. In these cases, hyperphosphorylated Rb both sequesters the pro-apoptotic activity of pp32 and is unable to correctly regulate E2F mediated gene transcription, allowing proliferation of tumor cells. Targets for the inhibition of the activity of the SET complex also comprise any member of the acidic nuclear phosphoprotein family, Anp32a-h, or isoform thereof that comprise the SET complex as described herein.

"Nucleases", "DNA nucleases", or "deoxyribonucleases", as defined herein, are the enzymes essential for maintaining genomic stability and are involved in processes such as DNA replication, repair and recombination. Nucleases have selective affinity for single-stranded (ss) or double-stranded (ds) DNA. They differ in their mode of action (5'-3' or 3'-5' direction) and their main reaction products (5' mono- or dinucleotides and 3' mononucleotides). As defined herein, an "endonuclease" is one of two classes of DNA nucleases, and hydrolyses the deoxyribose phosphodiester backbone within the DNA strand. An "exonuclease", as defined herein, is one of two classes of DNA nucleases, and hydrolyses the phosphodiester bonds at the DNA ends. Exonucleases may be autonomous or non-autonomous. Autonomous exonucleases hydrolyse their target sequences independently and may also assist DNA polymerases lacking this activity (e.g., Polα) to increase their fidelity under normal conditions or in cases of genotoxic cell stress.

"TREX1", "AGS1", "AGS5", "CRV", "DKFZp434J0310", "DRN3", or "HERNS" (Entrez GeneID: 11277) as defined herein, refers to the component of the SET complex that is the most abundant DNA 3'-5' exonuclease in mammalian cells, and is an autonomous non-processive 3'-5' DNA-specific exonuclease with a preference for ssDNA or mispaired 3' termini. The gene encoding TREX1 consists of a single exon and encodes a protein of 314 amino acids. Sequence homology places TREX1 in the DnaQ 3'-5' exonuclease family. The characteristic features of this family of exonucleases are three conserved sequence motifs, Exo I, Exo II and Exo III, which form the active site of the enzyme. Recent crystal structures of murine Trex1 with DNA17 demonstrate a dimer with the active sites on opposing surfaces, allowing the potential for concurrent interaction with two 3' DNA ends. These structures demonstrate close similarity with another DnaQ 3'-5' exonuclease, the Escherichia coli DNA polymerase I. In addition to these three exonuclease motifs, TREX1 has a highly hydrophobic carboxyl-terminal region which is predicted to form a transmembrane helix. Deletion mutagenesis has demonstrated that this region is important in intracellular localization but has no role in the catalytic function. The TREX1 protein also contains a proline-rich sequence (PPII helix). This motif has been reported to play a crucial role in protein-protein interactions, specifically with Src homology 3, WW and EVH1 domains. The structure of TREX1 indicates that the PPII helix is surface exposed and available for protein interactions. This has been hypothesized to account for the interaction of TREX1 with the SET complex17. "TREX2" is a TREX1 homologue with ~40% amino acid sequence identity with TREX1. TREX2 is also an autonomous DNA 3'-5' exonuclease, important for cell proliferation. TREX2 lacks the ~75 amino acid carboxyl-terminal hydrophobic domain found in TREX1, which is responsible for intracellular localization and contains the non-repetitive proline-rich region that plays a crucial role in protein-protein interactions. TREX2 contains a conserved DNA binding loop positioned adjacent to the active site that has a sequence distinct from the corresponding loop in the TREX1 enzyme. Analysis has indicated that TREX1 has a significant preference for particular DNA sequences and that this correlates with exonuclease activity. This exonuclease function, in addition to slight homology with known editing enzymes, indicates that a DNA-editing role in DNA replication or gap filling during DNA repair.

As described herein, TREX1 is a component of the SET complex. This protein complex is involved in granzyme A-mediated cell death, a caspase-independent pathway which involves ssDNA damage. The killer lymphocyte associated protease, granzyme A, causes mitochondrial damage and superoxide generation that induces nuclear translocation of the SET complex. It then cleaves the NM23-H1 inhibitor, SET, freeing NM23-H1 to make a ssDNA cut (introduces a DNA nick) that is then extended by TREX1. Cells with silenced TREX1 are relatively resistant to apoptotic cell death but remain sensitive to the caspase-activating granzyme B.

GzmA destroys the SET protein and releases Nm23-H1 from the SET complex, and then, Nm23-H1 can function as a nuclease in the nucleus. "NM23-H1", "AWD", "EC 2.7.4.6", "GAAD", "NB", "NBS", "NDPK-A", "NDPKA", "NM23", or "OTTHUMP00000174772", (Entrez GeneID: 4830), as defined herein, refers to the component of the SET complex that is a protein with a molecular weight of 18 kDa that is ubiquitously expressed in most cellular compartments. Nm23-H1 is a multifunctional enzyme that is highly conserved in many eukaryotic cells. This protein has various enzymatic functions such as nucleotide diphosphate kinase, histidine/aspartic acid-specific protein kinase, serine protein kinase, and granzyme-A activated DNase activities. To acquire enzymatic activities, Nm23-H1 necessarily undergoes hetero- or homo-hexameric oligomerization. As a NTP supplier, Nm23-H1 regulates the ratio of nucleoside triphosphate: nucleoside diphosphate for sustaining cellular homeostasis. A nucleotide trans-phosphorylation activity covalently transfers the γ-phosphate from a nucleoside triphosphate to a nucleoside diphosphate. For example, GTP is used as a source of energy for protein biosynthesis, and is necessary for the activation of G-protein mediated signal transduction. As the binding partners of Nm23-H1 have shown to be involved in G-coupled protein signal transduction, Nm23-H1 plays a role of cellular GTP supplier in G-coupled protein signal transduction. Many substrates of Nm23-H1 can exist in a cell, including, but not limited to, aldolase-C, by phosphorylating the aspartic acid residue; its own active site via autophosphorylation of the Nm23-H1 histidine residue; and serine phosphorylation (S392, S434) of KSR. Phosphorylated Nm23-H1 appears to increase the activity of the serine protein kinase, which can phosphorylate other substrates such as KSR (kinase suppressor of ras) involved in the Ras-Raf-MEK-Erk signal cascade.

As used herein, "base excision repair" (BER) refers to the primary DNA repair pathway that corrects base lesions that arise due to oxidative, alkylation, deamination, and depurinatiation/depyrimidination damage. BER facilitates the repair of damaged DNA via two general pathways—short-patch and long-patch. The short patch BER pathway leads to a repair tract of a single nucleotide. Alternatively, the long-patch BER pathway produces a repair tract of at least two nucleotides. The BER pathway is initiated by a DNA glycosylase, which recognizes and catalyzes the removal of damaged bases. The completion of the BER pathway is accomplished by the coordinated action of at least three additional enzymes. These downstream enzymes carry out strand incision, gap-filling and ligation. The core base excision repair pathway requires the function of only four proteins: these proteins include a DNA glycosylase, an AP endonuclease or AP DNA lyase, a DNA polymerase, and a DNA ligase. The first step in BER is the recognition of a damaged base by a DNA glycosylase. After recognition of the damaged base by the appropriate DNA glycosylase, this glycosylase catalyzes the cleavage of an N-glycosidic bond, effectively removing the damaged base and creating an apurinic or apyrmidinic site (AP site). The DNA backbone is cleaved by either a DNA AP endonuclease or a DNA AP lyase—an activity present in some glycosylases. AP endonuclease activity creates a single-stranded DNA nick 5' to the AP site, contrasting with the nick being created 3' to the AP site as resulting from DNA AP lyase activity. The newly created nick is processed by the AP endonuclease, creating a single-nucleotide gap in the DNA. Importantly, the gap created contains a 3'-hydroxyl and a 5'-phosphate, substrates compatible with the downstream enzymatic reactions in BER. A DNA polymerase fills in the gap with the correct nucleotide. Finally, a DNA ligase completes the repair process and restores the integrity of the helix by sealing the nick. two different enzymatic activities are capable of cleaving the DNA at the AP site. The first activity described is carried out by an AP endonuclease which incises the DNA 5' to the AP site, creating a 5' sugar moiety which must be processed by a DNA polymerase to allow for DNA ligation. Alternatively, the AP site is incised by an AP lyase, often associated with a bifunctional DNA glycosylase. This lyase activity creates a DNA nick containing a 3' sugar moiety which requires further processing by a DNA polymerase in order to provide a suitable substrate for a DNA ligase. As described herein, core "base excision repair enzymes" that are useful as targets for the methods and compositions of the present invention, include, but are not limited to: OGG1 (8-oxoguanine-DNA glycosylase; Entrez GeneID: 4968); NTHL1, (nth endonuclease III-like 1; Entrez GeneID: 4913); NEIL1 (Entrez GeneID: 79661), NEIL2 (Entrez GeneID: 252969), NEIL3 (Entrez GeneID: 55247) (nei endonuclease VIII-like); MUTYH, (Entrez GeneID: 4598; muty homolog); MPG, (N-methylpurine-DNA glycosylase; Entrez GeneID: 4350); UNG (uracil-DNA glycosylase; Entrez GeneID: 7374); SMUG1, (single-strand-selective monofunctional uracil-DNA glycosylase; Entrez GeneID: 23583); TDG, (thymine-DNA glycosylase; Entrez GeneID: 6996); MBD4, (methyl-CpG binding domain protein 4; Entrez GeneID: 8930); APEX1, (APEX nuclease 1; Entrez GeneID: 328); POLB (DNA polymerase; Entrez GeneID: 5423); FEN1, (flap structure-specific endonuclease 1; Entrez GeneID: 2237); XRCC1 (X-ray repair complementing defective repair in Chinese hamster cells 1; Entrez GeneID: 12828); and LIG3 (DNA ligase; Entrez GeneID: 3980).

As defined herein, "APE1", "APEN", "APEX", "APX", "EC 4.2.99.18", "HAP1", "OTTHUMP00000163988", or "REF-1" refers to the component of the SET complex that is a base excision repair (BER) endonuclease. APE1 is the major AP endonuclease in human cells, and splice variants have been found. APE1 recognizes the apurinic/apyrimidinic (AP) sites that occur frequently in DNA molecules through spontaneous hydrolysis, or by the activities of DNA damaging agents or by DNA glycosylases that remove specific abnormal bases. AP sites are pre-mutagenic lesions that can prevent normal DNA replication. Class II AP endonucleases, such as APE1, cleave the phosphodiester backbone and the catalytic activity involves the C—O—P bond 3' to the apurinic or apyrimidinic site in DNA being broken by a beta-elimination reaction, leaving a 3'-terminal unsaturated sugar and a product with a terminal 5'-phosphate. APE1 repairs oxidative DNA damages in vitro, and has a role in protection against cell lethality and suppression of mutations. APE1 can remove the blocking groups from the 3'-termini of the DNA strand breaks generated by ionizing radiations and bleomycin.

Other related aspects of the invention provide a method for increasing autointegration of retroviral nucleic acid comprising contacting a cell infected with a retrovirus with an inhibitor of a base excision repair enzyme. Other related aspects of the invention provide a method for decreasing retroviral nucleic acid integration in a cell comprising contacting a cell infected with a retrovirus with an inhibitor of a base excision repair enzyme. In some embodiments of these aspects and all other aspects described herein, one or more base excision repair enzymes are inhibited using the methods and compositions described herein. In some embodiments, the base excision repair enzyme being inhibited is selected from the group consisting of OGG1, NTHL1, NEIL1, NEIL2, NEIL3, MUTYH, MPG, UNG, SMUG1, TDG, MBD4, APEX1, POLB, FEN1, XRCC1, and LIG3. In some embodiments, the method further comprises inhibiting one or more components of the SET complex. In such embodiments, a component of the SET complex is selected from the group consisting of APE1, NM23-H1, TREX1, SET, HMGB2, and Pp32

Inhibitors of Components of the SET Complex and Base Excision Repair Enzymes

The components of the SET complex, and any sequence or domain mediating their SET complex activity, as described herein, are targets for the methods and compositions described herein. Accordingly, one aspect of the invention provides a method for increasing autointegration of retroviral nucleic acid comprising contacting a cell infected with a retrovirus with an effective amount of an inhibitor of a component of the SET complex, whereby autointegration of retroviral nucleic acid is increased in the cell relative to the cell prior to or in the absence of such contacting. In some embodiments, a component of the SET complex is selected from the group consisting of APE1, NM23-H1, TREX1, SET, HMGB2, and Pp32. In some embodiments, one or more components of the SET complex are inhibited. In some embodiments, the method further comprises inhibiting one or more base excision repair enzymes. In some embodiments, the base excision repair enzyme being inhibited is selected from the group consisting of OGG1, NTHL1, NEIL1, NEIL2, NEIL3, MUTYH, MPG, UNG, SMUG1, TDG, MBD4, APEX1, POLB, FEN1, XRCC1, and LIG3.

In connection with contacting a cell with an inhibitor of a component of the SET complex, "increasing autointegration of retroviral nucleic acid" in a cell indicates that retroviral nucleic acid autointegration is at least 5% higher in populations treated with an inhibitor of a component of the SET complex, than in a comparable, control population, wherein no inhibitor of a component of the SET complex is present. It is preferred that the percentage of retroviral nucleic acid autointegration in a population treated with a component of the SET complex is at least 5% higher, at least 7.5% higher, at least 10% higher, at least 20% higher, at least 30% higher, at least 40% higher, at least 50% higher, at least 60% higher, at least 70% higher, at least 80% higher, at least 90% higher, at least 1-fold higher, at least 2-fold higher, at least 5-fold higher, at least 10 fold higher, at least 100 fold higher, at least 1000-fold higher, or more than a control treated population of comparable size and culture conditions. It is most preferred that autointegration is increased to the point where no productive infection, or at least, no host genomic integration occurs. The term "control treated population" is used herein to describe a population of cells that has been treated with identical media, viral induction, nucleic acid sequences, temperature, confluency, flask size, pH, etc., with the exception of the addition of the SET complex inhibitor.

In connection with "increasing autointegration of retroviral nucleic acid", any assay that measures the retroviral nucleic acid autointegration products can be used in the methods of the invention. In one such embodiment, the assay used to measure autointegration of retroviral nucleic acid comprises a nested quantitative PCR assay. For the avoidance of doubt, an example of such a nested quantitative PCR assay that can be used comprises the following steps: Briefly, mitochondrial DNA, late RT and 2-LTR circles in extrachromosomal DNA fractions are analyzed by qPCR using MIT+/

MIT−, MH531/MH532 and AE2948/AE2949 primers, respectively (sequences below). β-Globin DNA is similarly measured in chromosomal DNA fractions using β-Globin+/β-Globin−primers. Integrated HIV DNA is also measured in chromosomal fractions, but by Alu-PCR followed by nested qPCR using AE989/AE990 primers. Autointegration products are measured using a two-step nested PCR: Step 1 is a semiquantitative PCR using 200 ng extrachromosomal DNA, 1×PCR buffer, 1.5 mM MgCl$_2$, 0.2 µM of each primer (PBS−, NY200/A+, NY199/B−), 0.2 mM dNTP and 1.5 U Platinum Taq polymerase (Invitrogen) in a 25 µL reaction volume. PCR program is 94° C./5 min, 24 cycles of 95° C./30 s-60° C./30 s-72° C./3 products from Step 1 are then diluted 1:100 for use in Step 2. Step 2 is a qPCR assay using AE989/AE990 primers (M. C. Shun et al., Genes Dev 21, 1767 (2007)). Primer sequences for use in the above assay include:

```
SEQ ID NO: 15: MIT+:
5'GACGTTAGGTCAAGGTGTAG-3';

SEQ ID NO: 16: MIT-:
5'-CAACTAAGCACTCTACTCTC-3';

SEQ ID NO: 17 MH531 (late RT forward):
5'-TGTGTGCCCGTCTGTTGTGT-3';

SEQ ID NO: 18 MH532 (late RT reverse):
5'-GAGTCCTGCGTCGAGAGAGC-3';

SEQ ID NO: 19 AE2948 (2-LTR forward):
5'-AACTAGGGAACCCACTGCTTAAG-3';

SEQ ID NO: 20 AE2949 (2-LTR reverse):
5'-TCCACAGATCAAGGATATCTTGTC-3';

SEQ ID NO: 21 β-Globin+:
5'-GAAGAGCCAAGGACAGGTAC-3';

SEQ ID NO: 22 β-Globin-:
5'-AAGCAATAGATGGCTCTGCC-3';

SEQ ID NO: 23 PBS-:
5'-TTTCCGGTCCCTGTTCGGGCGCCA-3';

SEQ ID NO: 24 Alu:
5'-TCCCAGCTACTCGGGAGGCTGAGG-3';

SEQ ID NO: 25 AE989 (R):
5'-TCTGGCTAGCTAGGGAACCCA-3';

SEQ ID NO: 26 AE990 (U5):
5'-CTGACTAGGATGGTCTGAGG-3';

SEQ ID NO: 27 NY199/primer B-:
5'-CTACCTTGTTATGTCCTGCTTG-3';
and

SEQ ID NO: 28 NY200/primer A+:
5'-CTCTACAGCACTTGGCACTAGC-3'.
```

Another aspect of the present invention relates to methods of decreasing retroviral nucleic acid integration into a host cell genome. In one embodiment of this aspect and all other aspects described herein, the method comprises contacting a cell infected with a retroviral nucleic acid with an effective amount of an inhibitor of a component of the SET complex, whereby retroviral nucleic acid integration is decreased in the cell relative to the cell prior to such contacting. In some embodiments, a component of the SET complex is selected from the group consisting of APE1, NM23-H1, TREX1, SET, HMGB2, and Pp32. One or more components of the SET complex may be targeted according to the methods of the present invention. In some embodiments, the method further or alternatively comprises inhibiting one or more base excision repair enzymes. In some embodiments, the base excision repair enzyme being inhibited is selected from the group consisting of OGG1, NTHL1, NEIL1, NEIL2, NEIL3, MUTYH, MPG, UNG, SMUG1, TDG, MBD4, APEX1, POLB, FEN1, XRCC1, and LIG3.

In connection with contacting a cell with an inhibitor of a component of the SET complex, "decreasing retroviral nucleic acid integration" in a cell indicates that retroviral nucleic acid integration is at least 5% lower in populations treated with an inhibitor of a component of the SET complex, than in a comparable, control population, wherein no inhibitor of a component of the SET complex is present. It is preferred that the percentage of retroviral nucleic acid integration in a population treated with an inhibitor of a component of the SET complex is at least 5% lower, at least 7.5% lower, at least 10% lower, at least 20% lower, at least 30% lower, at least 40% lower, at least 50% lower, at least 60% lower, at least 70% lower, at least 80% lower, at least 90% lower, at least 95% lower, at least 99%, at least 99.5% lower, at least 99.9% or more than a control treated population of comparable size and culture conditions. The term "control treated population" is used herein to describe a population of cells that has been treated with identical media, viral induction, nucleic acid sequences, temperature, confluency, flask size, pH, etc., with the exception of the addition of the inhibitor of a component of the SET complex.

Another aspect of the present invention relates to methods of decreasing provirus formation in a cell. In one embodiment of this aspect and all other aspects described herein, the method comprises contacting a cell or cell population infected with a retrovirus with an effective amount of an inhibitor of a component of the SET complex, whereby provirus formation is decreased in the cell or cell population relative to the cell prior to or in the absence of such contacting. In some embodiments, a component of the SET complex is selected from the group consisting of APE1, NM23-H1, TREX1, SET, HMGB2, and Pp32. One or more components of the SET complex may be targeted according to the methods of the present invention. In some embodiments, the method further or alternatively comprises inhibiting one or more base excision repair enzymes. In some embodiments, the base excision repair enzyme being inhibited is selected from the group consisting of OGG1, NTHL1, NEIL1, NEIL2, NEIL3, MUTYH, MPG, UNG, SMUG1, TDG, MBD4, APEX1, POLB, FEN1, XRCC1, and LIG3.

In connection with contacting a cell with an inhibitor of a component of the SET complex, "decreasing provirus formation" in a cell indicates that provirus formation is at least 5% lower in populations treated with an inhibitor of a component of the SET complex, than in a comparable, control population, wherein no inhibitor of a component of the SET complex is present. It is preferred that the percentage of provirus formation in a population treated with an inhibitor of a component of the SET complex is at least 5% lower, at least 7.5% lower, at least 10% lower, at least 20% lower, at least 30% lower, at least 40% lower, at least 50% lower, at least 60% lower, at least 70% lower, at least 80% lower, at least 90% lower, at least 95% lower, at least 99%, at least 99.5% lower, at least 99.9%, or more than a control treated population of comparable size and culture conditions. The term "control treated population" is used herein to describe a population of cells that has been treated with identical media, viral induction, nucleic acid sequences, temperature, confluency, flask size, pH, etc., with the exception of the addition of the inhibitor of a component of the SET complex.

In one aspect of this invention, and all other aspects described herein, an "inhibitor" of a component of the SET complex or a base excision repair enzyme, can function in a competitive or non-competitive manner, and can function by interfering with the expression, binding, and/or activity of any component of the SET complex or a base excision repair enzyme.

An "inhibitor of a component of the SET complex" can target one or more, and any combination thereof, of APE1, NM23-H1, TREX1, SET, HMGB2, and PP32. Any of a number of different approaches can be taken to inhibit SET complex expression or activity. A SET complex inhibitor includes any chemical or biological entity that, upon treatment of a cell, a population of cells, results in inhibition of the retroviral integration into a host nucleic acid or genome, or inhibition of retroviral autointegration caused by activation of SET complex in response to cellular or viral signals. Inhibitors of components of the SET complex include, but are not limited to, small molecules, antibodies or antigen-binding antibody fragments, peptides, intrabodies, aptamers, antisense constructs, RNA interference agents, and ribozymes.

Similarly, as used herein, an "inhibitor of a base excision repair enzyme" can target one or more, and any combination thereof, of OGG1, NTHL1, NEIL1, NEIL2, NEIL3, MUTYH, MPG, UNG, SMUG1, TDG, MBD4, APEX1, POLB, FEN1, XRCC1, and LIG3. Any of a number of different approaches can be taken to inhibit the activity of a base excision repair enzyme. A base excision repair enzyme inhibitor includes any chemical or biological entity that, upon treatment of a cell, results in inhibition of the retroviral integration into a host nucleic acid or genome, or inhibition of retroviral autointegration caused by activation of the base excision repair pathway in response to cellular or viral signals. Inhibitors of base excision repair enzymes include, but are not limited to, small molecules, antibodies or antigen-binding antibody fragments, peptides, intrabodies, aptamers, antisense constructs, RNA interference agents, and ribozymes.

In one embodiment of the invention and all aspects described herein, the inhibitor of a component of the SET complex is an antibody or antigen-binding fragment thereof, a small molecule, a peptide, or a nucleic acid. Alternatively and preferably, the inhibitor of a component of the SET complex is a specific RNA interference agent, or a vector encoding said specific RNA interference agent. In one embodiment, one or more specific RNA interference agent target(s) one or more, and any combination thereof, of APE1, NM23-H1, TREX1, SET, HMGB2, and PP32. In one further embodiment, the RNA interference agent comprises one or more of the nucleotide sequences of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:9.

As used herein, the term "small molecule" refers to a chemical agent including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

As used herein, "peptides inhibitors" can include for example mutated proteins, genetically modified proteins, peptides, synthetic peptides, recombinant proteins, chimeric proteins, antibodies, humanized proteins, humanized antibodies, chimeric antibodies, modified proteins and fragments thereof.

Antibody Inhibitors of the SET Complex:

Antibodies that specifically bind one or more components of the SET complex can be used for the methods and compositions of the invention. Antibodies, or antigen binding fragments thereof, to individual components of the SET complex, i.e., APE1, NM23-H1, TREX1, SET, HMGB2, and PP32, are both commercially available and can be raised by one of skill in the art using well known methods. The SET complex inhibitory activity of a given antibody, or, for that matter, any inhibitor of a component of the SET complex, can be assessed using methods known in the art or described herein. For example, an antibody that inhibits a component of the SET complex will cause an increase in autointegration of retroviral nucleic acid in an infected cell. Alternatively, any assay known to one of ordinary skill in the art that measures activity of the SET complex, or activity of the component of the SET complex being targeted by the antibody can be used.

Antibody inhibitors to components of the SET complex can include polyclonal and monoclonal antibodies and antigen-binding derivatives or fragments thereof. Well known antigen binding fragments include, for example, single domain antibodies (dAbs; which consist essentially of single VL or VH antibody domains), Fv fragment, including single chain Fv fragment (scFv), Fab fragment, and F(ab')2 fragment. Methods for the construction of such antibody molecules are well known in the art.

Thus, an "antibody" that can be used according to the methods described herein includes complete immunoglobulins, antigen binding fragments of immunoglobulins, as well as antigen binding proteins that comprise antigen binding domains of immunoglobulins. Antigen binding fragments of immunoglobulins include, for example, Fab, Fab', F(ab')2, scFv and dAbs. Modified antibody formats have been developed which retain binding specificity, but have other characteristics that may be desirable, including for example, bispecificity, multivalence (more than two binding sites), and compact size (e.g., binding domains alone). Single chain antibodies lack some or all of the constant domains of the whole antibodies from which they are derived. Therefore, they can overcome some of the problems associated with the use of whole antibodies. For example, single-chain antibodies tend to be free of certain undesired interactions between heavy-chain constant regions and other biological molecules. Additionally, single-chain antibodies are considerably smaller than whole antibodies and can have greater permeability than whole antibodies, allowing single-chain antibodies to localize and bind to target antigen-binding sites more efficiently. Furthermore, the relatively small size of single-chain antibodies makes them less likely to provoke an unwanted immune response in a recipient than whole antibodies. Multiple single chain antibodies, each single chain having one VH and one VL domain covalently linked by a first peptide linker, can be covalently linked by at least one or more peptide linker to form multivalent single chain antibodies, which can be monospecific or multispecific. Each chain of a multivalent single chain antibody includes a variable light chain fragment and a variable heavy chain fragment, and is linked by a peptide linker to at least one other chain. The peptide linker is composed of at least fifteen amino acid residues. The maximum number of linker amino acid residues is approximately one hundred. Two single chain antibodies can be combined to form a diabody, also known as a bivalent dimer. Diabodies have two chains and two binding sites, and can be monospecific or bispecific. Each chain of the diabody includes a VH domain connected to a VL domain. The domains are connected with linkers that are short enough to prevent pairing between domains on the same chain, thus driving the pairing between complementary domains on different chains to recreate the two antigen-binding sites. Three single chain antibodies can be combined to form triabodies, also known as trivalent trimers. Triabodies are constructed with the amino acid terminus of a VL or VH domain directly fused to the carboxyl terminus of a VL or VH domain, i.e., without any linker sequence. The triabody has three Fv heads with the polypeptides arranged in a cyclic, head-to-tail fashion. A possible conformation of the triabody is planar with the three binding sites located in a plane at an angle of 120 degrees from one another. Triabodies can be monospecific, bispecific or trispecific. Thus, antibodies useful in the methods described herein include, but are not limited to, naturally occurring antibodies, bivalent fragments such as (Fab')2, monovalent fragments such as Fab, single chain antibodies, single chain Fv (scFv), single domain antibodies, multivalent single chain antibodies, diabodies, triabodies, and the like that bind specifically with an antigen.

Antibodies can also be raised against a polypeptide or portion of a polypeptide by methods known to those skilled in the art. Antibodies are readily raised in animals such as rabbits or mice by immunization with the gene product, or a fragment thereof. Immunized mice are particularly useful for providing sources of B cells for the manufacture of hybridomas, which in turn are cultured to produce large quantities of monoclonal antibodies. Antibody manufacture methods are described in detail, for example, in Harlow et al., 1988. While both polyclonal and monoclonal antibodies can be used in the methods described herein, it is preferred that a monoclonal antibody is used where conditions require increased specificity for a particular protein.

Nucleic Acid Inhibitors of the SET Complex:

A "nucleic acid inhibitor", as described herein, can be RNA or DNA, and can be single or double stranded, and can be selected, for example, from a group including: nucleic acid encoding a protein of interest, oligonucleotides, nucleic acid analogues, for example peptide-nucleic acid (PNA), pseudo-complementary PNA (pc-PNA), locked nucleic acid (LNA) etc. Such nucleic acid sequences include, for example, but are not limited to, nucleic acid sequence encoding proteins, for example that act as transcriptional repressors, aptamers, antisense molecules, ribozymes, small inhibitory nucleic acid sequences, for example but are not limited to RNAi, shRNAi, siRNA, micro RNAi (mRNAi), antisense oligonucleotides etc.

A powerful approach for inhibiting the expression of selected target polypeptides is through the use of RNA interference agents. RNA interference (RNAi) uses small interfering RNA (siRNA) duplexes that target the messenger RNA encoding the target polypeptide for selective degradation. siRNA-dependent post-transcriptional silencing of gene expression involves cleaving the target messenger RNA molecule at a site guided by the siRNA. "RNA interference" is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) J. of Virology 76(18):9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of a gene encoding a component of the SET complex, i.e., APE1, NM23-H1, TREX1, SET, HMGB2, and PP32 As used herein, "inhibition of a gene encoding a component of the SET complex" includes any decrease in expression or protein activity or level of a target gene encoding a component of the SET complex or protein encoded by said gene, i.e., APE1, NM23-H1, TREX1, SET, HMGB2, and PP32, as compared to a situation wherein no RNA interference has been introduced. The decrease will be of at least 5%, 7.5%, 10%, 20%, 30%, 40%, 50%, 60%, 70%, 80%, 90%, 95% or 99% or more as compared to the expression of a target gene encoding a component of the SET complex or the activity or level of the protein encoded by said target gene in the absence of targeting by an RNA interfering agent.

The terms "RNA interference agent" and "RNA interference" as they are used herein are intended to encompass those forms of gene silencing mediated by double-stranded RNA, regardless of whether the RNA interfering agent comprises an siRNA, miRNA, shRNA or other double-stranded RNA molecule. "Short interfering RNA" (siRNA), also referred to herein as "small interfering RNA" is defined as an RNA agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand may precede the nucleotide loop structure and the antisense strand may follow. These shRNAs may be contained in plasmids, viral vectors, including, e.g., adenoviral vectors, AAV vectors, among them, retroviral and lentiviral vectors and expressed from, for example, the pol III U6 promoter, or another promoter (see, e.g., Stewart, et al. (2003) RNA April; 9(4):493-501, incorporated by reference herein in its entirety). The target gene or sequence of the RNA interfering agent may be a cellular gene or genomic sequence, e.g. the SET or NM23-H1 sequence. An siRNA may be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs. Preferably, the siRNA is identical to its target. The siRNA preferably targets only one sequence. Each of the RNA interfering agents, such as siRNAs, can be screened for potential off-target effects by, for example, expression profiling. Such methods are known to one skilled in the art and are described, for example, in Jackson et al. Nature Biotechnology 6:635-637, 2003. In addition to expression profiling, one may also screen the potential target sequences for similar sequences in the sequence databases to identify potential sequences which may have off-target effects. For example, according to Jackson et al. (Id.), 15, or perhaps as few as 11 contiguous nucleotides, of sequence identity are sufficient to direct silencing of non-targeted transcripts. Therefore, one may initially screen the proposed siRNAs to avoid potential off-target silencing using the sequence identity analysis by any known sequence comparison methods, such as BLAST. siRNA sequences are chosen to maximize the uptake of the antisense (guide) strand of the siRNA into RISC and thereby maximize the ability of RISC to target mRNA for degradation. This can be accomplished by scanning for sequences that have the lowest free energy of binding at the 5'-terminus of the antisense strand. The lower free energy leads to an enhancement of the unwinding of the 5'-end of the antisense strand of the siRNA duplex, thereby ensuring that the antisense strand will be taken up by RISC and direct the sequence-specific cleavage of a SET complex component mRNA, i.e., APE1, NM23-H1, TREX1, SET, HMGB2, and PP32 mRNA. siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatizes with a variety of groups. Other useful RNA derivatives incorporate nucleotides having modified carbohydrate moieties, such as 2'O-alkylated residues or 2'-O-methyl ribosyl derivatives and 2'-O-fluoro ribosyl derivatives. The RNA bases may also be modified. Any modified base useful for inhibiting or interfering with the expression of a target sequence may be used. For example, halogenated bases, such as 5-bromouracil and 5-iodouracil can be incorporated. The bases may also be alkylated, for example, 7-methylguanosine can be incorporated in place of a guanosine residue. Non-natural bases that yield successful inhibition can also be incorporated. The most preferred siRNA modifications include 2'-deoxy-2'-fluorouridine or locked nucleic acid (LAN) nucleotides and RNA duplexes containing either phosphodiester or varying numbers of phosphorothioate linkages. Such modifications are known to one of ordinary skill in the art and are described, for example, in Braasch et al., Biochemistry, 42: 7967-7975, 2003. Most of the useful modifications to the siRNA molecules can be introduced using chemistries established for antisense oligonucleotide technology. Preferably, the modifications involve minimal 2'-O-methyl modification, preferably excluding such modification. Modifications also preferably exclude modifications of the free 5'-hydroxyl groups of the siRNA.

In some embodiments, the RNA interference agent is delivered or administered in a pharmaceutically acceptable carrier. Additional carrier agents, such as liposomes, can be added to the pharmaceutically acceptable carrier. In another embodiment, the RNA interference agent is delivered by a vector encoding small hairpin RNA (shRNA) in a pharmaceutically acceptable carrier to the cells in an organ of an individual. The shRNA is converted by the cells, after transcription, into siRNA capable of targeting a component of the SET complex, i.e., APE1, NM23-H1, TREX1, SET, HMGB2, and/or PP32.

In some embodiments, the RNA interference agent used in the methods described herein are taken up actively by cells in vivo following intravenous injection, e.g., hydrodynamic injection, without the use of a vector, illustrating efficient in vivo delivery of the RNA interfering agents. One method to deliver the siRNAs is catheterization of the blood supply vessel of a target organ.

Other strategies for delivery of the RNA interference agents, e.g., the siRNAs or shRNAs used in the methods of the invention, may also be employed, such as, for example, delivery by a vector, e.g., a plasmid or viral vector, e.g., a lentiviral vector. Such vectors can be used as described, for example, in Xiao-Feng Qin et al. Proc. Natl. Acad. Sci. U.S.A., 100: 183-188. In one embodiment, the vector delivering the RNA interference agent is a regulatable vector, such as tetracycline inducible vector. Methods described, for example, in Wang et al. Proc. Natl. Acad. Sci. 100: 5103-5106, using pTet-On vectors (BD Biosciences Clontech, Palo Alto, Calif.) can be used. As used herein, the term "vector" refers to a nucleic acid molecule capable of transporting another nucleic acid to which it has been linked. One type of vector is a "plasmid", which refers to a circular double stranded DNA loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Moreover, certain vectors are capable of directing the expression of genes to which they are operatively linked. Such vectors are referred to herein as "recombinant expression vectors", or more simply "expression vectors." In general, expression vectors of utility in recombinant DNA techniques are often in the form of plasmids. However, the invention is intended to include other forms of expression vectors, such as viral vectors (e.g., replication defective retroviruses, lentiviruses, adenoviruses and adeno-associated viruses), which serve equivalent functions. In one embodiment, lentivirus vectors are used to deliver one or more siRNA molecules to a cell. To the extent that a lentiviral vector is genetically engineered not to integrate into a host cell genome, such vectors can still be used in a method of inhibiting productive retroviral infection or for promoting autointegration.

Within an expression vector, "operably linked" is intended to mean that the nucleotide sequence of interest is linked to the regulatory sequence(s) in a manner which allows for expression of the nucleotide sequence (e.g., in an in vitro transcription/translation system or in a target cell when the vector is introduced into the target cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). Furthermore, the RNA interfering agents may be delivered by way of a vector comprising a regulatory sequence to direct synthesis of the siRNAs of the invention at specific intervals, or over a specific time period. It will be appreciated by those skilled in the art that the design of the expression vector can depend on such factors as the choice of the target cell, the level of expression of siRNA desired, and the like.

The expression vectors of the invention can be introduced into target cells to thereby produce siRNA molecules of the present invention. In one embodiment, a DNA template, e.g., a DNA template encoding the siRNA molecule directed against the mutant allele, may be ligated into an expression vector under the control of RNA polymerase III (Pol III), and delivered to a target cell. Pol III directs the synthesis of small, noncoding transcripts which 3' ends are defined by termination within a stretch of 4-5 thymidines. Accordingly, DNA templates may be used to synthesize, in vivo, both sense and antisense strands of siRNAs which effect RNAi (Sui, et al. (2002) PNAS 99(8):5515).

Other delivery methods include delivery of the RNA interfering agents, e.g., the siRNAs or shRNAs of the invention, using a basic peptide by conjugating or mixing the RNA interfering agent with a basic peptide, e.g., a fragment of a TAT peptide, mixing with cationic lipids or formulating in particles. The RNA interference agents, e.g., the siRNAs targeting the APE1, NM23-H1, TREX1, SET, HMGB2, and PP32 mRNA, may be delivered singly, or in combination with other RNA interference agents, e.g., siRNAs, such as, for example siRNAs directed to other cellular genes. The siRNAs for inhibiting one or more components of the SET complex, i.e., APE1, NM23-H1, TREX1, SET, HMGB2, and PP32, may also be administered in combination with other pharmaceutical agents which are used to treat or prevent diseases or disorders associated with the retrovirus infecting the cell. Synthetic siRNA molecules, including shRNA molecules, can be obtained using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (see, e.g., Elbashir, S. M. et al. (2001) Nature 411:494-498; Elbashir, S. M., W. Lendeckel and T. Tuschl (2001) Genes & Development 15:188-200; Harborth, J. et al. (2001) J. Cell Science 114:4557-4565; Masters, J. R. et al. (2001) Proc. Natl. Acad. Sci., USA 98:8012-8017; and Tuschl, T. et al. (1999) Genes & Development 13:3191-3197). Alternatively, several commercial RNA synthesis suppliers are available including, but not limited to, Proligo (Hamburg, Germany), Dharmacon Research (Lafayette, Colo., USA), Pierce Chemical (part of Perbio Science, Rockford, Ill., USA), Glen Research (Sterling, Va., USA), Chem-Genes (Ashland, Mass., USA), and Cruachem (Glasgow, UK). As such, siRNA molecules are not overly difficult to synthesize and are readily provided in a quality suitable for RNAi. In addition, dsRNAs can be expressed as stem loop structures encoded by plasmid vectors, retroviruses and lentiviruses (Paddison, P. J. et al. (2002) Dev. 16:948-958; McManus, M. T. et al. (2002) RNA 8:842-850; Paul, C. P. et al. (2002) Nat. Biotechnol. 20:505-508; Miyagishi, M. et al. (2002) Nat. Biotechnol. 20:497-500; Sui, G. et al. (2002) Proc. Natl. Acad. Sci., USA 99:5515-5520; Brummelkamp, T. et al. (2002) Cancer Cell 2:243; Lee, N. S., et al. (2002) Nat. Biotechnol. 20:500-505; Yu, J. Y., et al. (2002) Proc. Natl. Acad. Sci., USA 99:6047-6052; Zeng, Y., et al. (2002) Mol. Cell 9:1327-1333; Rubinson, D. A., et al. (2003) Nat. Genet. 33:401-406; Stewart, S. A., et al. (2003) RNA 9:493-501). These vectors generally have a polIII promoter upstream of the dsRNA and can express sense and antisense RNA strands separately and/or as a hairpin structures. Within cells, Dicer processes the short hairpin RNA (shRNA) into effective siRNA. The targeted region of the siRNA molecule of the present invention can be selected from a given target gene sequence, e.g., a SET coding sequence, beginning from about 25 to 50 nucleotides, from about 50 to 75 nucleotides, or from about 75 to 100 nucleotides downstream of the start codon. Nucleotide sequences may contain 5' or 3' UTRs and regions nearby the start codon. One method of designing a siRNA molecule of the present invention involves identifying the 23 nucleotide sequence motif AA(N19)TT (where N can be any nucleotide) (SEQ ID NO: 54) and selecting hits with at least 25%, 30%, 35%, 40%, 45%, 50%, 55%, 60%, 65%, 70% or 75% G/C content. The "TT" portion of the sequence is optional. Alternatively, if no such sequence is found, the search may be extended using the motif NA(N21), where N can be any nucleotide. In this situation, the 3' end of the sense siRNA may be converted to TT to allow for the generation of a symmetric duplex with respect to the sequence composition of the sense and antisense 3' overhangs. The antisense siRNA molecule may then be synthesized as the complement to nucleotide positions 1 to 21 of the 23 nucleotide sequence motif. The use of symmetric 3' TT overhangs may be advantageous to ensure that the small interfering ribonucleoprotein particles (siRNPs) are formed with approximately equal ratios of sense and antisense target RNA-cleaving siRNPs (Elbashir et al. (2001) supra and Elbashir et al. 2001 supra). Analysis of sequence databases, including but not limited to the NCBI, BLAST, Derwent and GenSeq as well as commercially available oligosynthesis companies such as Oligoengine®, may also be used to select siRNA sequences against EST libraries to ensure that only one gene is targeted.

Delivery of RNA Interfering Agents:

Methods of delivering RNA interference agents, e.g., an siRNA, or vectors containing an RNA interference agent, to the target cells, e.g., CD4 T lymphocytes or other desired target cells, for uptake include injection of a composition containing the RNA interference agent, e.g., an siRNA, or directly contacting the cell, e.g., a CD4 T lymphocyte, with a composition comprising an RNA interference agent, e.g., an siRNA targeting a component of the SET complex, i.e., APE1, NM23-H1, TREX1, SET, HMGB2, or PP32. In another embodiment, RNA interference agent, e.g., an siRNA may be injected directly into any blood vessel, such as vein, artery, venule or arteriole, via, e.g., hydrodynamic injection or catheterization. Administration may be by a single injection or by two or more injections. The RNA interference agent is delivered in a pharmaceutically acceptable carrier. One or more RNA interference agents may be used simultaneously. In one embodiment, only one siRNA that targets a component of the SET complex is used. In one embodiment, specific cells are targeted with RNA interference, limiting potential side effects of RNA interference caused by non-specific targeting of RNA interference. The method can use, for example, a complex or a fusion molecule comprising a cell targeting moiety and an RNA interference binding moiety that is used to deliver RNA interference effectively into cells. For example, an antibody-protamine fusion protein when mixed with siRNA, binds siRNA and selectively delivers the siRNA into cells expressing an antigen recognized by the antibody, resulting in silencing of gene expression only in those cells that express the antigen. In some embodiments, the cells being targeted express the CD4 antigen. The siRNA or RNA interference-inducing molecule binding moiety is a protein or a nucleic acid binding domain or fragment of a protein, and the binding moiety is fused to a portion of the targeting moiety. The location of the targeting moiety can be either in the carboxyl-terminal or amino-terminal end of the construct or in the middle of the fusion protein. A viral-mediated delivery mechanism can also be employed to deliver siRNAs to cells in vitro and in vivo as described in Xia, H. et al. (2002) Nat Biotechnol 20(10):1006). Plasmid- or viral-mediated delivery mechanisms of shRNA may also be employed to deliver shRNAs to cells in vitro and in vivo as described in Rubinson, D. A., et al. ((2003) Nat. Genet. 33:401-406) and Stewart, S. A., et al. ((2003) RNA 9:493-501). The RNA interference agents, e.g., the siRNAs or shRNAs, can be introduced along with components that perform one or more of the following activities: enhance uptake of the RNA interfering agents, e.g., siRNA, by the cell, e.g., CD4 T lymphocytes or other cells, inhibit annealing of single strands, stabilize single strands, or otherwise facilitate delivery to the target cell and increase inhibition of the target gene, e.g., APE1, NM23-H1, TREX1, SET, HMGB2, and/or Pp32. The dose of the particular RNA interfering agent will be in an amount necessary to effect RNA interference, e.g., post translational gene silencing (PTGS), of the particular target gene, thereby leading to inhibition of target gene expression or inhibition of activity or level of the protein encoded by the target gene.

In some embodiments of the aspects of the invention described herein, the cell infected with a retrovirus is contacted ex vivo or in vitro. In some embodiments, the cell being contacted expresses the cell-surface antigen CD4. In some embodiments, the cell expressing CD4 is a CD4 T lymphocyte. In some embodiments, the cell expressing CD4 is a macrophage.

As used herein, "CD4" refers to the glycoprotein expressed on the surface of T helper cells, regulatory T cells, monocytes, macrophages, and dendritic cells, and encoded by the CD4 gene. CD4 is the primary receptor used by HIV-1 to gain entry into host cells. Such host cells may be any cell expressing CD4. HIV-1 attaches to CD4 with a viral envelope protein known as gp120. The binding to CD4 creates a shift in the conformation of gp120 allowing HIV-1 to bind to two other surface receptors on the host cell, the chemokine receptors CCR5 or CXCR4, depending on whether HIV is infecting a macrophage or T-helper cell. Following a structural change in another viral protein (gp41), HIV inserts a fusion peptide into the host cell that allows the outer membrane of the virus to fuse with the cell membrane.

"CD4 T cell", "CD4 lymphocyte", or "CD4 T lymphocyte", as used herein, refers to the subset of T lymphocytes expressing the CD4 glycoprotein. CD4 T cells may also be referred to as T helper cells, effector T cells or Th cells. CD4 cells are involved in activating and directing other immune cells, and are particularly important in the immune system. They are essential in determining B cell antibody class switching, in the activation and growth of cytotoxic T cells, and in maximizing bactericidal activity of phagocytes such as macrophages. CD4 cells recognize antigen in the context of Class II Major Histocomptability Molecules (MHC Class II).

A "macrophage", as used herein, refers to a subset of immune cells derived from monocytes, that participate in both non-specific defense (or innate immunity) as well as help initiate specific defense mechanisms (or cell-mediated immunity) of vertebrate animals. Their role is to phagocytose (engulf and then digest) cellular debris and pathogens either as stationary or mobile cells, and to stimulate lymphocytes and other immune cells to respond to the pathogen. Macrophages can be identified using a variety of techniques. In a non-limiting example, a macrophage target of the present invention is identified by CD68 immunohistochemical staining.

Treatment of Retroviral Infections

As disclosed herein, it is an object of the present invention to provide methods and compositions for the treatment of a retroviral infection in a subject in need thereof.

Accordingly, one aspect of the invention provides a method for the treatment of an infection by a retrovirus in a subject in need thereof, comprising administering to the subject an effective amount of composition comprising one or more inhibitors of the SET complex, thereby decreasing retroviral infection and/or replication in said subject. Accordingly, in some embodiments the subject in need has been diagnosed with an infection with a retrovirus. In a further embodiment, the retrovirus is a lentivirus. In one preferred embodiment, the lentivirus is HIV.

Another aspect of the invention provides a method for the treatment of infection by a human immunodeficiency virus (HIV) in a subject in need thereof, the method comprising administering to said subject in need an effective amount of a composition comprising a one or more inhibitors of a component of the SET complex, wherein said inhibitor decreases HIV infection and/or replication in said subject.

By "decreasing retroviral infection" is meant that productive infection by a retrovirus is reduced or decreased or inhibited. The methods described herein exploit and target the retrovirus's approach to avoid autointegration resulting in essentially the "suicide" of the retrovirus. This approach relies on infection of the cell to the extent that the retroviral RNA genome is inserted into the cell and converted to double-stranded DNA. The dsDNA is then induced to autointegrate thereby destroying iys ability to integrate into the host cell's genome and result in productive infection whereby viral progeny are generated. Thus a "decrease" in retroviral infection induced by the methods described herein may not directly inhibit the initial infection of a cell, but will inhibit the proviral state and will inhibit the generation of viral progeny. The decrease in the proviral state and/or generation of viral progeny will be at least 10% lower, and preferably at least 20% lower, at least 30% lower, at least 40% lower, at least 50% lower, at least 60% lower, at least 70% lower, at least 80% lower, at least 90% lower, at least 95% lower, at least 99%, at least 99.5% lower, at least 99.9% or more, up to and including a 100% reduction (i.e., no productive infection). A "decrease" in retroviral infection can also refer then to a decrease in viral load, i.e., at least 10% lower, and preferably at least 20% lower, at least 30% lower, at least 40% lower, at least 50% lower, at least 60% lower, at least 70% lower, at least 80% lower, at least 90% lower, at least 95% lower, at least 99%, at least 99.5% lower, at least 99.9% or more, up to and including a 100% reduction (i.e., no viral load).

The term "subject" is intended to encompass a singular "subject" and plural "subjects" and includes, but is not limited to humans; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and bears. In some preferred embodiments, a subject in need thereof is a human.

The term "effective amount", as used herein, refers to the amount that is safe and sufficient to treat, lessen the likelihood of, or delay the progress of a retroviral infection. The effective amount can thus cure or result in amelioration of the symptoms of the retroviral infection, slow the course of disease progression resulting from retroviral infection, slow or inhibit a symptom of a retroviral infection, slow or inhibit the establishment of secondary symptoms of a retroviral infection or inhibit the development of a secondary symptom of a retroviral infection. The effective amount for the treatment of the retroviral infection depends on the type of retroviral infection to be treated, the severity of the symptoms, the subject being treated, the age and general condition of the subject, the mode of administration and so forth. Thus, it is not possible or prudent to specify an exact "effective amount". However, for any given case, an appropriate "effective amount" can be determined by one of ordinary skill in the art using only routine experimentation. In one embodiment, the effective amount is a "therapeutically effective amount" for the alleviation of the symptoms of the disease mediated by the retroviral infection or condition being treated. In another embodiment, the effective amount is a "prophylactically effective amount" for prophylaxis of the symptoms of the disease or condition being prevented. The term also includes the amount of active compound sufficient to inhibit retroviral nucleic acid integration and thereby elicit the response being sought (i.e., an "inhibition effective amount").

Of particular importance as a target for the methods and compositions of the present invention, is the human lentivirus known as "human immunodeficiency virus-1" or "HIV-1", also referred to herein as HTLV-III, LAV or HTLV-III/LAV, the etiological agent of the acquired immune deficiency syndrome (AIDS) and related disorders. (Barre-Sinoussi, et al., Science, 220:868-871 (1983); Gallo, et al., Science, 224:500-503 (1984); Levy, et al., Science, 225:840-842 (1984); Popovic, et al., Science, 224:497-500 (1984); Sarngadharan, et al., Science, 224:506-508 (1984); Siegal, et al., New England Journal of Medicine, 305:1439-1444 (1981)). AIDS is characterized by a long asymptomatic period followed by the progressive degeneration of the immune system and the central nervous system. Studies of the HIV-1 virus indicate that replication is highly regulated, and both latent and lytic infection of the CD4 positive helper subset of T-lymphocytes occur in tissue culture (Zagury, et al., Science, 231:850-853 (1986)). The expression of the virus in infected patients also appears to be regulated as the titer of infectious virus remains low throughout the course of the disease. Molecular studies of the replication and genomic organization of HIV-1 show that it encodes a number of genes (Ratner, et al., Nature, 313:277-284 (1985); Sanchez-Pescador, et al., Science, 227:484-492 (1985); Muesing, et al., Nature, 313:450-457 (1985); Wain-Hobson, et al., Cell, 40:9-17 (1985)). Three of the genes, the gag, pol and env genes are common to all retroviruses. The genome also encodes additional genes that are not common to most retroviruses, the tat, rev (formerly referred to as art), nef, vif, vpr and vpu genes (Sodroski, et al., Science, 231:1549-1553 (1986); Arya, et al.,. Science, 229:69-73 (1985); Sodroski, et al., Nature, 321:412-417 (1986); Feinberg, et al., Cell, 46:807-817 (1986); Haseltine, Journal of Acquired Immune Deficiency Syndrome, 1:217-240 (1988); Cohen, et al., Nature, 334:532-534 (1988); Wong-Staal, et al., AIDS Res. and Human Retro Viruses, 3:33-39 (1987)). Nucleotide sequences from viral genomes of other retroviruses, particularly HIV-2 and simian immunodeficiency viruses, SIV (previously referred to as STLV-III), also contain the structural genes including env as well as regulatory sequences such as tat, rev and nef (Guyader, et al., Nature, 326:662-669 (1987); Chakrabarti, et al., Nature, 328:543-547 (1987)). These three HIV viruses share a similar genetic organization, even though there can be sequence variations.

Infection with HIV leads, in most cases, to a progressive decline in the number and functions of CD4+ T cells with the eventual appearance of clinical manifestations of cellular immunodeficiency, such as opportunistic infections and malignancies, i.e., AIDS (Fauci, et al., Ann. Int. Med., 100: 92-99 (1984)). The entry of HIV-1 into the target cells requires, in association with the CD4 molecule, the simultaneous virus binding to a chemokine receptor. CXCR4 and CCR5, members of the chemokine receptor family of proteins, serve as secondary coreceptors for HIV-1 isolates that are tropic for T-cell lines or macrophages, respectively. Deng et al. (1996) Nature 381:661-6; Doranz et al. (1996) Cell 86:1149-59; and Berger et al. (1998) Nature 391:240. CXCR4 or CCR5, in conjunction with CD4, form a functional cellular receptor for entry of certain strains of HIV into cells. Reports indicated that the viral envelope glycoprotein gp120 interacts directly with chemokine receptors generally at a step following CD4 binding. Lapham et al. (1996) Science 274:602-605; Moore (1997) Science 276:51; Wu et al. (1996) Nature 384:179-183; and Hesselgesser et al. (1997) Current Biology 7:112-121. Envelope variants will selectively interact with either CXCR4 or CCR5.

HIV-1 strains transmitted in vivo generally use CCR5 (CCR5 viruses). Fenyo et al. (1998) Nature 391:240; Samson et al. (1996) Nature 382:722-5; Shankarappa et al. (1999) J. Virol. 73:10489-502; and Scarlatti et al. (1997) Nature Med. 3:1259-65. These viruses typically infect macrophages and primary CD4+ lymphocytes, and do not form syncytia in vitro. Bjorndal et al. (1997) J. Virol. 71:7478-87. These viruses are said to be macrophage tropic (M-tropic). After primary HIV-1 infection, viral populations are usually characterized by molecular heterogeneity. Shankarappa et al. (1999); and Glushakova et al. (1999) J. Clin. Invest. 104:R7-R11. Years after chronic infection is established, strains using CXCR4 emerge in about 50% of infected individuals (Berger et al. (1998); Scarlatti et al. (1997); Koot et al. (1993); and Connor et al. (1997) J. Exp. Med. 185:621-8). CXCR4 strains not only infect primary T-lymphocytes but also replicate in T-cell lines and induce syncytia (Bjorndal et al. (1997)). These viruses are said to be T-cell tropic (T-tropic). This difference in cell tropism correlates with disease progression. During HIV infection, strains isolated from individuals early in the course of their infection are usually M-tropic, while viruses isolated from approximately 50% of individuals with advanced immunodeficiency also include viruses that are T-tropic.

CXCR4 strains have been shown to have a striking influence on HIV-1 disease progression. Cytopathicity toward the general CD4+ T cell population in lymphoid tissue is associated with the use of CXCR4. Glushakova et al. (1999). The emergence of CXCR4 virus is predictive of rapid depletion of CD4+ cells and acceleration of HIV-1 disease progression. Berger et al. (1998); Scarlatti et al. (1997); and Connor et al. (1997). (1997). A recent analysis of HIV-1 coreceptor use in infected individuals suggested that the rapid CD4+ cell decline is related to the ability of CXCR4 viruses to infect an expanded spectrum of crucial target cells as compared to CCR5 strains. Blaak et al. (2000) Proc. Natl. Acad. Sci. USA 97:1269-74. In vitro results suggest that selective blockade of CXCR4 receptors may prevent the switch from the less pathogenic CCR5 strains to the more pathogenic CXCR4 strains. Este et al. (1999) J. Virol. 73:5577-85. Coreceptor use plays a critical role in viral tropism, pathogenesis, and disease progression.

For the purpose of the inhibition of HIV replication, the prophylaxis or treatment of HIV infection, or the prophylaxis or treatment or delay in the onset of AIDS, the compositions of the present invention can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds can, for example, be administered orally, transmucosally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically-acceptable carriers, adjuvants and vehicles. In preferred embodiments, the compositions are administered as an oral preparation. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in Remington's Pharmaceutical Sciences, 18.sup.th edition, edited by A. R. Gennaro, Mack Publishing Co., 1990 and in Remington—The Science and Practice of Pharmacy, 21.sup.st edition, Lippincott Williams & Wilkins, 2005.

The methods of treatment according to the present invention ameliorate one or more symptoms in a subject associated with the retroviral infection by preventing retroviral nucleic acid replication or decreasing the amount of retroviral nucleic acid replication in a subject, or preventing a productive infection. In some embodiments the retroviral infection is an HIV infection. In some embodiments, the symptoms associated with the HIV infection comprise the symptoms associated with the development of AIDS. The symptoms associated with HIV infection can include, but are not limited to, reduction in CD4+ T cell numbers, pain (peripheral neuropathy); fever, cough, and other cold/flu symptoms; night sweats; diarrhea, nausea, and other indigestion symptoms; lymph swelling or other immunological symptoms; weight loss and loss of appetite; candida in the mouth; secondary bacterial and/or viral infections; elevated liver enzymes; reduction in central nervous system and brain function; depression; overall reduced immunity; AIDS-related complications (ARC), including, but not limited to, progressive generalization lymphadenia (PGL), Kaposi's sarcoma, Pneumocystis carinii pneumonia, cataplectic purpura thrombocytopenica; AIDS related neurological syndromes, including, but not limited to, AIDS dementia complications, AIDS encephalopathy, disseminated sclerosis ortropical paraplegia; as well as anti HIV antibody-positive and HIV-positive syndrome including that in silent patients.

The invention also provides, in part, a composition comprising one or more inhibitors of a component of the SET complex and a pharmaceutically acceptable carrier or diluent. In one embodiment of all aspects of the invention described herein, said composition is administered by injection, infusion, instillation, or ingestion for use in the methods of the invention.

As used herein, the term "pharmaceutically acceptable", and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. Each carrier must also be "acceptable" in the sense of being compatible with the other ingredients of the formulation. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. The pharmaceutical formulation contains a compound of the invention in combination with one or more pharmaceutically acceptable ingredients. The carrier can be in the form of a solid, semi-solid or liquid diluent, cream or a capsule. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the invention that will be effective in the treatment of a particular disorder or condition will depend on the nature of the disorder or condition, and can be determined by standard clinical techniques. The phrase "pharmaceutically acceptable carrier or diluent" means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body.

As used herein, "administered" refers to the placement of an inhibitor of a component of the SET complex into a subject by a method or route which results in at least partial localization of the inhibitor at a desired site. An agent which inhibits a component of the SET complex can be administered by any appropriate route which results in effective treatment in the subject, i.e. administration results in delivery to a desired location in the subject where at least a portion of the composition delivered, i.e., at least one agent which inhibits a component of the SET complex, is active in the desired site for a period of time. The period of time the inhibitor is active depends on the half life in vivo after administration to a subject, and can be as short as a few hours, e. g. twenty-four hours, to a few days, to as long as several years. Modes of administration include injection, infusion, instillation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion.

The methods and compositions of the present invention, i.e., inhibitors of components of the SET complex, may be used in combination with one or more anti-HIV agents known to be useful in the treatment of HIV infection or AIDS. An "anti-HIV agent" is any agent which is directly or indirectly effective in the inhibition of HW integrase or another enzyme required for HIV replication or infection, the treatment or prophylaxis of HIV infection, and/or the treatment, prophylaxis or delay in the onset of AIDS. It is understood that an anti-HIV agent is effective in treating, preventing, or delaying the onset of HIV infection or AIDS and/or diseases or conditions arising therefrom or associated therewith. For example, the compounds of this invention may be effectively administered, whether at periods of pre-exposure and/or post-exposure, in combination with effective amounts of one or more HIV antivirals, immunomodulators, antiinfectives, or vaccines useful for treating HIV infection or AIDS, such as those disclosed in Table 1 of WO 01/38332 or in the Table in WO 02/30930. Suitable HIV antivirals for use in combination with the compounds described herein for antiretroviral therapy can include, but are not limited to, HAART, protease inhibitors, fusion inhibitors, integrase inhibitors, co-receptor specific agents, 3TC, AZT, nevirapine, non-nucleoside analogue reverse transcriptase inhibitors and nucleoside analogue reverse transcriptase inhibitors. HAART can be three or more antiretroviral drugs in combination, including as examples regimens that have at least one protease inhibitor, or at least a reverse transcriptase inhibitor and a protease inhibitor; or at least two reverse transcriptase inhibitors with at least one protease inhibitor.

Typical HIV reverse transcriptase inhibitors for use in the present invention include nucleoside analogs, e.g., AZT (Zidovudine), ddi (didanosine), ddc (zalcitabine), D4T (stavudine), 3TC (lamivudine), tenofovir, Ziagen (abacavir), combivir (mix of AZT and 3TC), and non-nucleoside analogs, e.g., viramune (nevirapine), rescriptor (delavirdine), sustiva (efavirenz). Typical HIV protease inhibitors include invirase (saquinavir), norvir (ritonavir), atazanavir, crixivan (indinavir), viracept (nelfinavir), agenerase (amprenivir), kaletra (lopinavir and ritonavir) and fortovase (saquinavir in a soft gelatin form). Thus, HAART can also be "triple cocktail" therapy—a three drug regimen to combat HIV wherein one of the three drugs is usually a protease inhibitor (and the other two are usually reverse transcritase inhibitors). It will be understood that the scope of combinations of the compounds of this invention with HIV antivirals, immunomodulators, anti-infectives or vaccines is not limited to the foregoing substances or to the list in the above-referenced Tables in WO 01/38332 and WO 02/30930, but includes in principle any combination with any pharmaceutical composition useful for the treatment of HIV infection or AIDS. The HIV antivirals and other agents will typically be employed in these combinations in their conventional dosage ranges and regimens as reported in the art, including, for example, the dosages described in the Physicians' Desk Reference, 63.sup.th edition, Thomson PDR, 2009. The dosage ranges for a compound of the invention in these combinations are the same as those set forth above. It is understood that pharmaceutically acceptable salts of the compounds of the invention and/or the other agents (e.g., indinavir sulfate) can be used as well.

Screening for Inhibitors of SET Complex or Base Excision Repair Activity

As disclosed herein, also encompassed within the aspects of the present invention are methods for identifying "candidate agents" that inhibit SET complex or base excision repair functions (especially DNA-binding or DNA-metabolizing activity). In some embodiments, the method comprises the steps of: (a) discovering and identifying candidate agents that inhibit early stage retroviral replication; (b) screening of the identified candidate agents from step (a) by measuring stage-specific retroviral DNA products (reverse transcripts, autointegration) to identify candidate agents that specifically inhibit the autointegration step of retroviral infection; and (c) validating candidate agents that promote the autointegration step in clinically relevant conditions. In one embodiment, the retrovirus is a HIV.

In one embodiment, an assay for identifying candidate agents that inhibit SET complex or base excision repair functions is provided comprising the steps of: (i) Treating HeLa-CD4 cells with a library of test agents in 384-well format plates. Twenty-four hours after treatment, treated cells are infected with Vesicular Stomatitis Virus Glycoprotein (VSV-G) pseudotyped HIV-GFP virus for eight hours. GFP expression and cell count numbers are evaluated 24 hours post-infection using an automatic fluorescent microscope, or any other method known to one of ordinary skill in the art. Positive "hits" for step (i) will be identified based on a GFP fluorescence that is at least 5% lower, at least 7.5% lower, at least 10% lower, at least 20% lower, at least 30% lower, at least 40% lower, at least 50% lower, at least 60% lower, at least 70% lower, at least 80% lower, at least 90% lower, or more, up to, and including at least 100% lower (i.e., no infection) than a control treated population of comparable size and culture conditions, and in the absence of any significant change in corresponding cell number. The term "control treated population" is used herein to describe a population of cells that has been treated with identical media, viral induction, nucleic acid sequences, temperature, confluency, flask size, pH, etc., with the exception of the addition of the treatment. (ii) Using the top hits determined from step (i) and performing the same treatment-infection protocol as described in step (i) in 12-well format plates. Extrachromosomal DNA is isolated 10 hours post infection and reverse transcripts and autointegration products are measured by qPCR, or any other method known to one of ordinary skill in the art. Positive hits from the step (ii) are scored if autointegration levels in a well are at least 5% higher, at least 7.5% higher, at least 10% higher, at least 20% higher, at least 30% higher, at least 40% higher, at least 50% higher, at least 60% higher, at least 70% higher, at least 80% higher, at least 90% higher, at least 1-fold higher, at least 2-fold higher, at least 5-fold higher, at least 10 fold higher, at least 100 fold higher, at least 1000-fold higher, or more than a control treated population of comparable size and culture conditions, and in the absence of a significant change in reverse transcript level. The term "control treated population" is used herein to describe a population of cells that has been treated with identical media, viral induction, nucleic acid sequences, temperature, confluency, flask size, pH, etc., with the exception of the addition of the treatment. (iii) Top hits from step (iii) are validated using replication-competent HIV-IIIB viruses and a clinically relevant T-cell line, such as, for example, Jurkat cells. One surrogate marker of infectivity that is contemplated for use in the above-described method is determining the level of HIV Capsid protein (p24) in the media supernatant.

Candidate agents, or a library of candidate agents, that can be screened with methods of the present invention include polypeptides, β-turn mimetics, polysaccharides, phospholipids, hormones, prostaglandins, steroids, aromatic compounds, heterocyclic compounds, benzodiazepines, oligomeric N-substituted glycines, oligocarbamates, polypeptides, saccharides, fatty acids, steroids, purines, pyrimidines, derivatives, small molecules, siNA, siRNA, dsRNA, dsDNA, anti-senseDNA, nucleic acids, antibodies, polyclonal antibodies, monoclonal antibodies, structural analogs or combinations thereof. Some candidate agents are synthetic molecules, and others natural molecules.

Candidate agents are obtained from a wide variety of sources including libraries of synthetic or natural compounds. Combinatorial libraries can be produced for many types of compound that can be synthesized in a step-by-step fashion. Large combinatorial libraries of compounds can be constructed by the encoded synthetic libraries (ESL) method described in WO 95/12608, WO 93/06121, WO 94/08051, WO 95/35503 and WO 95/30642. Peptide libraries can also be generated by phage display methods (see, e.g., Devlin, WO 91/18980). Libraries of natural compounds in the form of bacterial, fungal, plant and animal extracts can be obtained from commercial sources or collected in the field. Known pharmacological agents can be subject to directed or random chemical modifications, such as acylation, alkylation, esterification, amidification to produce structural analogs.

Combinatorial libraries of peptides, nucleic acids, or other compounds can be fully randomized, with no sequence preferences or constants at any position. Alternatively, the library can be biased, i.e., some positions within the sequence are either held constant, or are selected from a limited number of possibilities. For example, in some cases, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, or to purines.

The candidate agents can be natural occurring proteins or their fragments. Such candidate agents can be obtained from a natural source, e.g., a cell or tissue lysate. Libraries of polypeptide candidate agents can also be prepared, e.g., from a cDNA library commercially available or generated with routine methods. The candidate agents can also be peptides, e.g., peptides of from about 5 to about 30 amino acids, with from about 5 to about 20 amino acids being preferred, and from about 7 to about 15 being particularly preferred. The peptides can be digests of naturally occurring proteins, random peptides, or "biased" random peptides. In some methods, the candidate agents are polypeptides or proteins.

The candidate agents can also be nucleic acids. Nucleic acid candidate agents can be naturally occurring nucleic acids, random nucleic acids, or "biased" random nucleic acids. For example, digests of prokaryotic or eukaryotic genomes can be similarly used as described above for proteins. In some embodiments, the candidate agent can be a member of an RNAi library.

In some preferred embodiments, the test agents are small molecules (e.g., molecules with a molecular weight of not more than about 1,000). Preferably, high throughput assays are adapted and used to screen for such small molecules.

Libraries of candidate agents to be screened with the claimed methods can also be generated based on structural studies of the SET complex or any of its components, i.e., APE1, NM23-H1, TREX1, SET, HMGB2, and Pp32. Such structural studies allow the identification of candidate agents that are more likely to bind to a component of the SET complex, i.e., APE1, NM23-H1, TREX1, SET, HMGB2, and Pp32. The three-dimensional structure of the SET complex or any of its components, i.e., APE1, NM23-H1, TREX1, SET, HMGB2, and Pp32 (e.g., any of their catalytic domains) can be studied in a number of ways, e.g., crystal structure and molecular modeling. Methods of studying protein structures using x-ray crystallography are well known in the literature. See Physical Bio-chemistry, (85-86). Computer modeling of a target protein (e.g., APE1, NM23-H1, TREX1, SET, HMGB2, and Pp32) provides another means for designing test agents for screening modulators of the target protein. Methods of molecular modeling have been described in the literature, e.g., U.S. Pat. No. 5,612,894 entitled "System and method for molecular modeling utilizing a sensitivity factor", and U.S. Pat. No. 5,583,973 entitled "Molecular modeling method and system". In addition, protein structures can also be determined by neutron diffraction and nuclear magnetic resonance (NMR).

As used in this specification and the appended claims, the singular forms "a", "an", and "the" include plural references unless the context clearly dictates otherwise. Thus for example, references to "the method" includes one or more methods, and/or steps of the type described herein and/or which will become apparent to those persons skilled in the art upon reading this disclosure and so forth. It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

As used herein, the term "comprising" means that other elements can also be present in addition to the defined elements presented. The use of "comprising" indicates inclusion rather than limitation. The term "consisting of" refers to compositions, methods, and respective components thereof as described herein, which are exclusive of any element not recited in that description of the embodiment. As used herein the term "consisting essentially of" refers to those elements required for a given embodiment. The term permits the presence of elements that do not materially affect the basic and novel or functional characteristic(s) of that embodiment of the invention.

EXAMPLES

Introduction

After the HIV-1 envelope fuses to the host cell membrane and uncoats, the viral genomic RNA is reverse transcribed within the reverse transcription complex (RTC) to double-stranded DNA (S. P. Goff, Nat Rev Microbiol 5, 253 (2007)). The RTC matures into the preintegration complex (PIC), which delivers the viral DNA to the nucleus for integration into a chromosome (Y. Suzuki, R. Craigie, Nat Rev Microbiol 5, 187 (2007)). The PIC may also sequester and protect the viral DNA from cellular DNA-modifying enzymes (K. Yoder et al., Proc Natl Acad Sci USA 103, 4622 (2006)) and from cytoplasmic DNA sensors (R. Medzhitov, Nature 449, 819 (2007)) that could trigger antiviral innate immunity. Surprisingly little is known about the host proteins that associate with the PIC and assist in HIV-1 integration.

Integration can be divided into three steps: (1) 3' processing (integrase (IN)-mediated hydrolysis of GT dinucleotides from HIV-1 DNA to produce reactive, recessed $CA_{OH}$-3' ends); (2) DNA strand transfer (IN-mediated insertion of the cleaved 3' ends into opposing strands of host chromosomal DNA); and (3) 5'-end joining (repair by host enzymes of the gaps between the 5'-ends of viral DNA and the chromosome) (A. Engelman, Curr Top Microbiol Immunol 281, 209 (2003)).

3'-processing makes the viral DNA vulnerable to the suicidal autointegration pathway known as (C. Shoemaker et al., J Virol 40, 164 (1981); Y. Li et al., J Virol 65, 3973 (1991)) in which the reactive CA ends attack sites within the viral DNA.

Herein we show that the SET complex and components thereof play an important role in the early phase of the HIV-1 lifecycle by inhibiting autointegration.

Results

Silencing SET Complex Proteins Inhibits HIV-I Infection

Knockdown of SET and/or NM23-H1 in HeLaCD4 cells reduced HIV-1$_{IIIB}$ infectivity 3 to 4-fold as assessed by p24 levels in culture supernatants (FIG. 1A or 1B). Although virion production was impaired, the virions produced from knockdown cells were equally infectious when applied in equivalent amounts (normalized by p24 level) to indicator TZM-b1 cells that express an HIV LTR-driven luciferase (Luc) reporter gene (FIG. 1H). This suggested that SET and NM23-H1 act early in the viral life cycle.

To focus on early events, cells were infected with an HIV-1-derived single-round reporter virus (HIV-Luc) pseudotyped with the vesicular stomatitis virus G (VSV-G) envelope glycoprotein (M. C. Shun et al., J Virol 81, 166 (2007)), and infection was assessed two days later by Luc activity. Knockdown of SET, NM23-H1, or both reduced Luc activity to 24%, 19%, and 15% of control levels, respectively (FIG. 1C). HIV-Luc activity was restored by expressing RNAi-insensitive SET (SET-in) in SET siRNA-treated cells (FIG. 1D). Single-round virus carrying the natural HIV-1 envelope glycoproteins was similarly inhibited by SET and/or NM23-H1 knockdown (FIG. 1I). Because inhibition was independent of the envelope glycoprotein, SET and NM23-H1 likely influenced post-entry steps.

SET can influence chromatin accessibility in its role as a histone chaperone and inhibitor of histone acetylation and DNA demethylation, and NM23-H1 enhances the transcription of some genes (D. Chowdhury and J. Lieberman, Annu Rev Immunol 26, 389 (2008)). It was tested whether knocking down SET and NM23-H1 inhibited transcription from the HIV-1 LTR in HeLaCD4 cells transfected with HIV-Luc plasmid DNA. There was no significant effect on reporter gene expression (FIG. 1E). Together these experiments indicate that SET and NM23-H1 act downstream of viral entry and before Tat-dependent transcription.

The SET protein is a component of at least two complexes—a ~150 kDa nuclear complex that contains SET and pp32 and some of their paralogues and the ~270-420 kDa ER-associated SET complex (P. J. Beresford et al., J Biol Chem 276, 43285 (2001); S. B. Seo et al., Cell 104, 119 (2001)). Because NM23-H1 knockdown interfered with HIV-1, we reasoned that the larger SET complex facilitated infection. In fact, knocking down the other members of this complex similarly reduced HIV-Luc activity (FIG. 1F).

To test whether SET and NM23-H1 enhance infection of other retroviruses, the effect of knocking down SET and NM23-H1 on SIV, MLV, and avian sarcoma virus (ASV) was tested using similar Luc reporter systems. SIV-Luc infectivity was inhibited by SET/NM23-H1 knockdown (although not as strongly as HIV-1), while MLV-Luc and ASV-Luc were largely unaffected (FIGS. 1F and 1G).

SET/NM23-H1 Knockdown Reduces Chromosomal Integration

Figure 2:
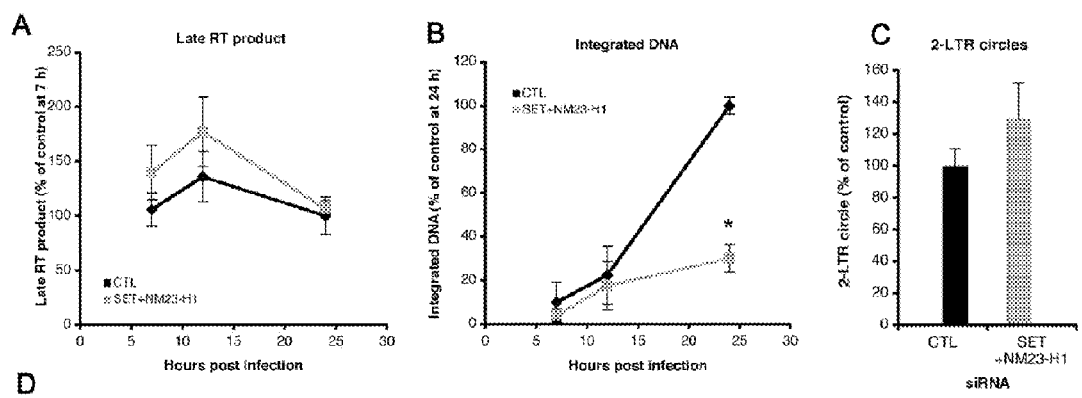
FIG. 2 demonstrates that HIV-1 integration is reduced in SET/NM23-H1 knockdown cells.
Figure 2:
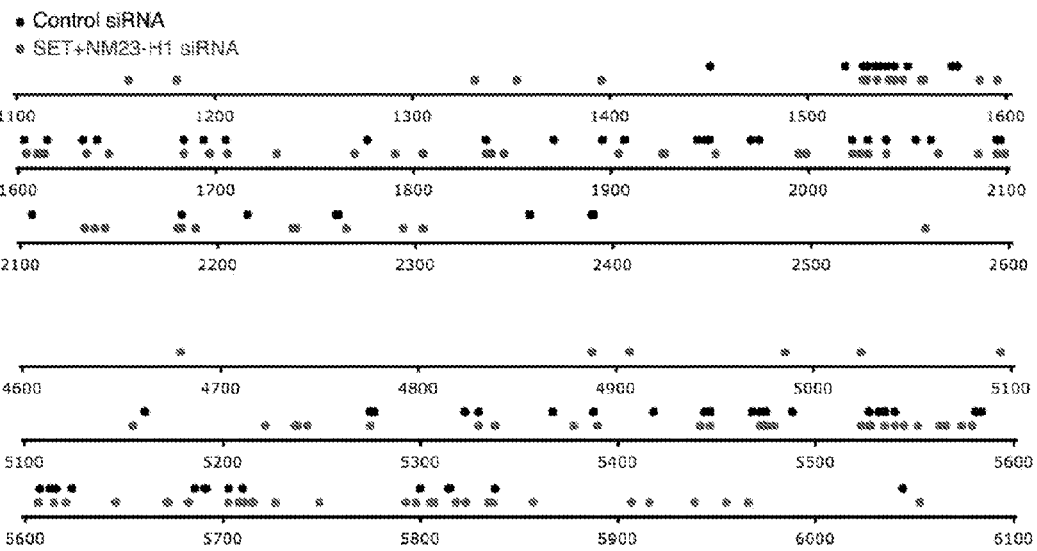

To pinpoint the block in the viral life cycle, we compared the effect of SET/NM23-H1 knockdown on stage-specific HIV-1 DNA products by quantitative PCR (qPCR) (S. L. Butler et al., Nat Med 7, 631 (2001); M. C. Shun et al., Genes Dev 21, 1767 (2007)). Late reverse transcription products (late RT) measured during the first day of infection were not significantly different in knockdown cells (FIG. 2A). In contrast, integrated HIV-1 DNA (quantified by nested Alu-PCR) was reduced by 3-fold 24 hr post infection (hpi) in SET/NM23-H1 knockdown cells (FIG. 2B). Two-long terminal repeat (2-LTR) circles were slightly, but not significantly, increased by the knockdown (FIG. 2C).

To understand why HIV-1 integration might be impaired, insertion sites were sequenced (M. C. Shun et al., Genes Dev 21, 1767 (2007)) using DNA isolated 24 hpi from control and SET/NM23-H1 knockdown cells. HIV-1 normally integrates preferentially into transcriptionally active chromatin (A. R. Schroder et al., Cell 110, 521 (2002); R. S. Mitchell et al., PLoS Biol 2, E234 (2004)). The frequency of integration within transcription units, CpG islands, and promoters was not significantly different in the knockdown cells (FIG. 2D). Although the DNA for the integration site analysis was isolated from the Hirt pellet, which is enriched for chromosomal DNA, a significant number of clones arose from autointegration. The proportion of autointegrants recovered from SET/NM23-H1 knockdown cells significantly exceeded the control, comprising 259 of 816 sequences (32%) vs 182 of 816 (22%) sequences (p<0.0001) (FIGS. 2D and 2E). The autointegration sites in the control and knockdown cells showed the same sequence preference as chromosomal integration, favoring insertion within GG dinucleotides (FIG. 2F) (M. C. Shun et al., Genes Dev 21, 1767 (2007)).

SET/NM23-H1 Knockdown Enhances Autointegration

Figure 3:
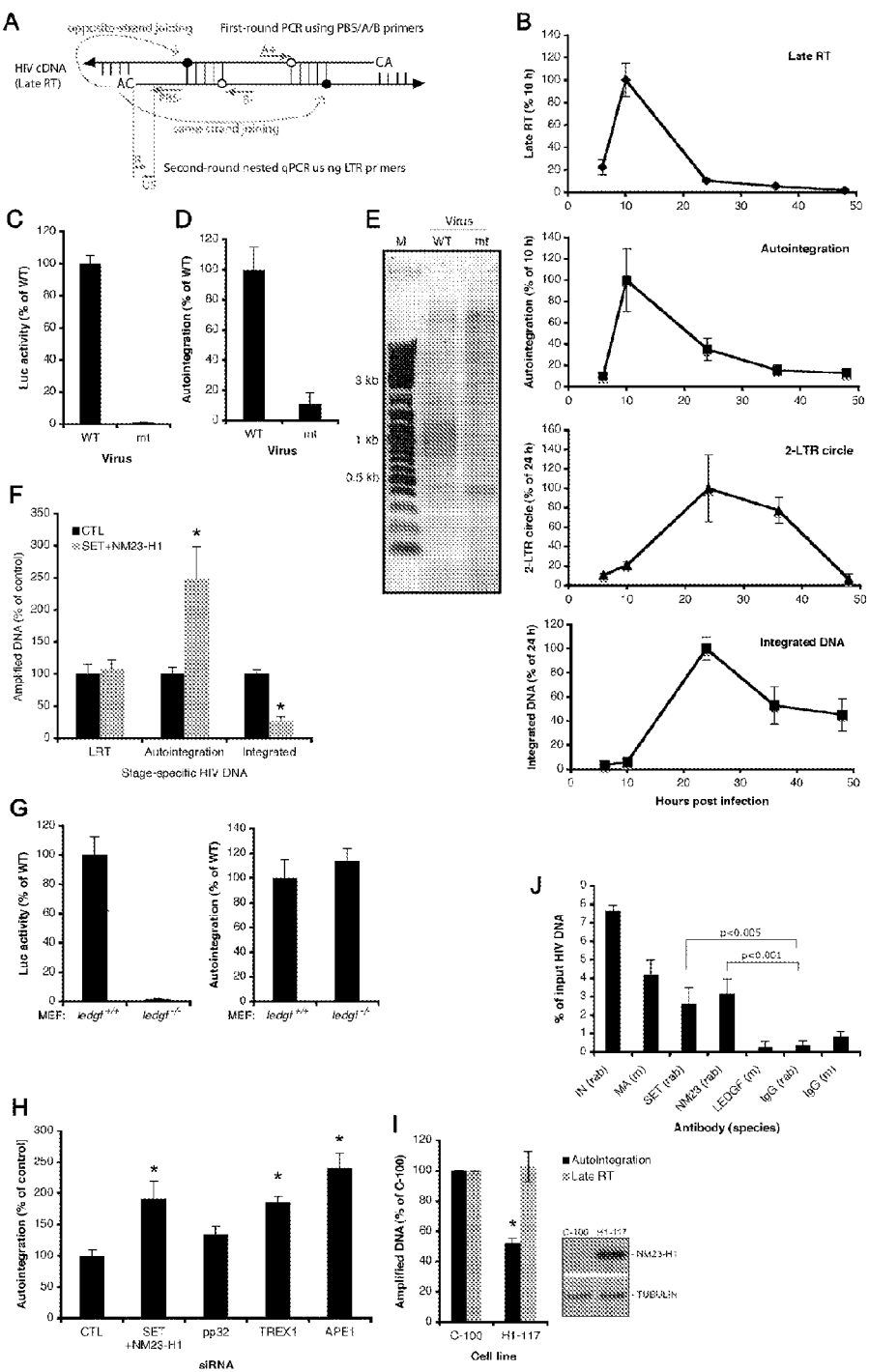
FIG. 3 demonstrates that the SET complex suppresses HIV-1 autointegration.
Figure 3:
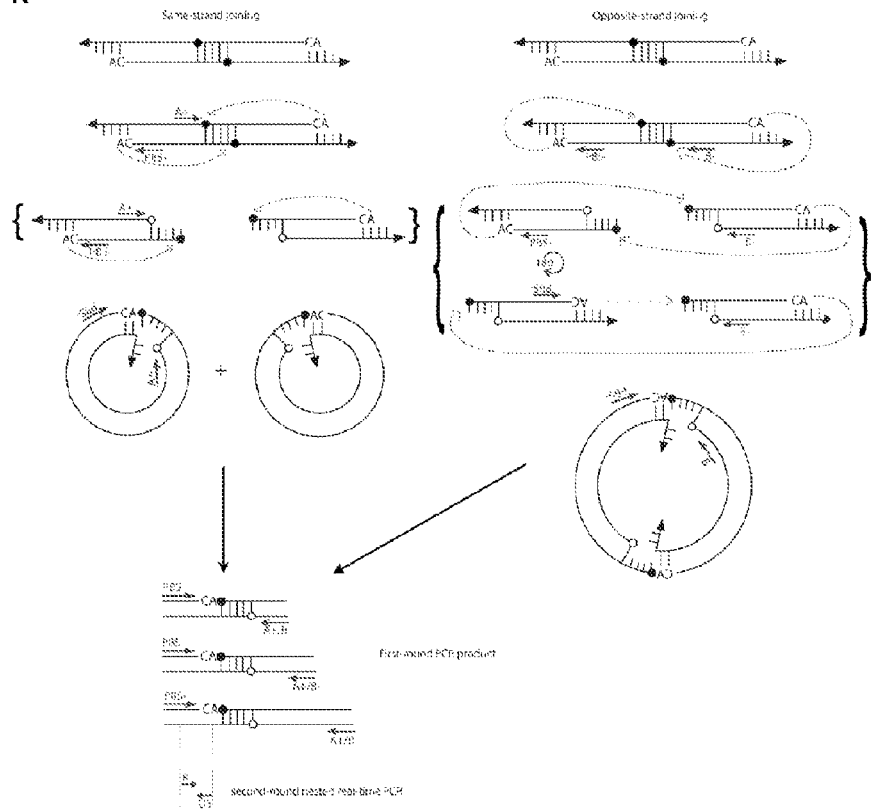
Figure 3:
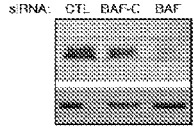
Figure 3:
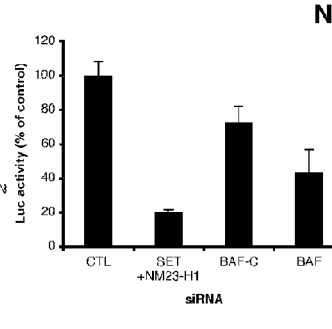
Figure 3:
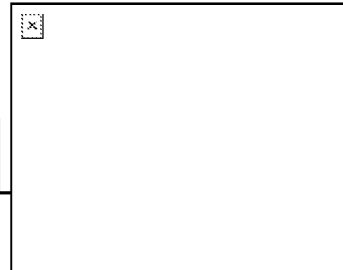
Figure 3:
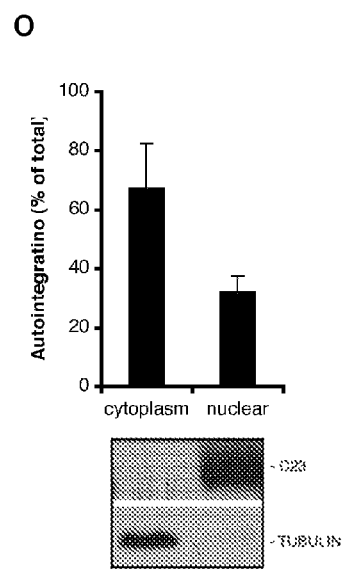

A nested qPCR autointegration assay (auto-PCR) was developed and designed to quantify and clone autointegration events from Hirt supernatant DNA. Three primers (PBS- (primer binding site), A+, and B−) were designed to detect integration of the minus strand U3 CA-3' end into either strand of viral DNA (FIGS. 3A and 3K). The first PCR round generates products that contain the upstream LTR of variable length depending on the distance between the site of autointegration and primer A+ or B−. The qPCR (second) round amplifies LTR sequences of a fixed length from diluted first-round PCR products. To validate the assay, we verified that first-round PCR using only PBS or A+ and B− primers amplified negligible amounts of LTR-containing DNA compared to reactions with all 3 primers.

Autointegration is expected to occur shortly after reverse transcription because 3' processing can happen soon after DNA synthesis (M. D. Miller et al., J Virol 71, 5382 (1997)). Auto-PCR and late RT DNAs both peaked 10 hpi, while 2-LTR circles and integrated DNA peaked 24 hpi (FIG. 3B). These kinetics support the specificity of the auto-PCR assay to detect autointegrants rather than 2-LTR circles. Since autointegration requires IN activity, HeLaCD4 cells were infected with HIV-Luc carrying either wild-type (WT) or active site mutant (D64N/D116N, mt) IN. As expected, auto-PCR product formation was significantly reduced following mt IN viral infection (FIG. 3D). First-round PCR products electrophoresed through agarose gels produced a smear migrating at ~1 kb from WT-infected cells while mt virus products had no appreciable DNA in this region (FIG. 3E). DNA from the regions corresponding to the 1 Kb smear were isolated, cloned, and sequenced. 21 of 30 clones from the WT viral infection contained an IN-processed U3 end (identified by loss of the GT dinucleotide from the unprocessed CAGT end). The processed U3 end joined to an internal viral sequence in 13 cases whereas the remaining 8 sequences contained only viral LTR sequences (Table 1). Only 5 of 30 clones from the mt IN virus infection contained any viral sequence and none contained a processed U3 end (Table 1). These results demonstrate that the auto-PCR assay predominantly amplifies autointegrated HIV-1 DNA.

TABLE 1

Autointegrant sequences recovered from WT and mt IN viral infections*.

| SEQ ID NO | Clone | DNA junction sequence† | Viral internal insertion site‡ | Comment |
|---|---|---|---|---|
| | | WT IN autointegrants | | |
| SEQ ID NO: 29 | 1-2 | . . . TTAGCCCTTCC<u>A</u>CCTACAATCC . . . | 4654 | U3-internal |
| SEQ ID NO: 30 | 1-5 | . . . TTAGCCCTTCC<u>A</u>AAAGATTAGT . . . | 5105 | U3-internal |
| SEQ ID NO: 31 | 1-7 | . . . TTAGCCCTTCC<u>A</u>GGAGAAAGAG . . . | 5263 | U3-internal |
| SEQ ID NO: 32 | 1-8 | . . . TTAGCCCTTCC<u>A</u>GTCTCCATAG . . . | 5293 | U3-internal |
| SEQ ID NO: 33 | 1-9 | . . . TTAGCCCTTCC<u>A</u>AAAGCAAAGA . . . | 5019 | U3-internal |
| SEQ ID NO: 34 | 1-14 | . . . TTAGCCCTTCC<u>A</u>GAAAGTACTA . . . | 5173 | U3-internal |
| SEQ ID NO: 35 | 1-15 | . . . TTAGCCCTTCC<u>A</u>CTAATCCAAA . . . | 5180 | U3-internal |
| SEQ ID NO: 36 | 1-16 | . . . TTAGCCCTTCC<u>A</u>GGAGAAAGAG . . . | 5263 | U3-internal |
| SEQ ID NO: 37 | 1-19 | . . . TTAGCCCTTCC<u>A</u>ATATAGTTAGT . . . | 5421 | U3-internal |
| SEQ ID NO: 38 | 1-21 | . . . TTAGCCCTTCC<u>A</u>GGCAGTAGTA . . . | 4970 | U3-internal |
| SEQ ID NO: 39 | 1-23 | . . . TTAGCCCTTCC<u>A</u>AAGTAGACCC . . . | 5330 | U3-internal |
| SEQ ID NO: 40 | 1-24 | . . . TTAGCCCTTCC<u>A</u>GTCTCCATAG . . . | 5293 | U3-internal |
| SEQ ID NO: 41 | 1-27 | . . . TTAGCCCTTCC<u>A</u>GTAATAACAA . . . | 5233 | U3-internal |
| SEQ ID NO: 42 | 1-3 | . . . TGAATAAAGA . . . AACAAGGTAG . . . | 4690-5467 | Internal only |
| SEQ ID NO: 43 | 1-12 | . . . TCCTCTGGAA . . . AACAAGGTAG . . . | 4951-5467 | Internal only |

TABLE 1-continued

Autointegrant sequences recovered from WT and mt IN viral infections*.

| SEQ ID NO | Clone | DNA junction sequence† | Viral internal insertion site‡ | Comment |
|---|---|---|---|---|
| SEQ ID NO: 44 | 1-30 | . . . ACTAATCCAA . . . AACAAGGTAG . . . | 5179-5467 | Internal only |
| | 1-1 | LTR only | n/a | |
| | 1-6 | LTR only | n/a | |
| | 1-10 | LTR only | n/a | |
| | 1-13 | LTR only | n/a | |
| | 1-20 | LTR only | n/a | |
| | 1-22 | LTR only | n/a | |
| | 1-25 | LTR only | n/a | |
| | 1-29 | LTR only | n/a | |
| mt IN autointegrants | | | | |
| SEQ ID NO: 45 | 2-17 | . . . GGGCAAGAAA . . . AACAAGGTAG . . . | 4509-5467 | Internal only |
| | 2-4 | LTR only | n/a | |
| | 2-8 | LTR only | n/a | |
| | 2-10 | LTR only | n/a | |
| | 2-18 | LTR only | n/a | |

*Clones that did not contain any viral sequence are not shown.
†The CA dinucleotide at the end of the cleaved U3 minus strand is underlined.
‡Number refers to position in reference HIV-1$_{NL4-3}$ strain.

With the auto-PCR assay validated, we compared autointegration and other stage-specific HIV-1 DNAs in control and SET/NM23-H1 knockdown cells (FIG. 3F). Late RT products were comparable 10 hpi as shown in FIG. 2A, whereas autointegration assayed at the same time increased 2.5 fold in SET/NM23-H1 knockdown cells ($p<0.01$). Chromosomal integration measured 24 hpi decreased 3-fold ($p<0.001$), as expected (FIG. 2B), in SET/NM23-H1 knockdown as compared to control cells. The corresponding increase in autointegration and decrease in chromosomal integration indicated that the integration defect is due to reduced available substrate because of suicidal autointegration.

Because increased autointegration occurred before chromosomal integration, it was unlikely that autointegration was secondary to failed chromosomal integration. To test directly whether autointegration might be an obligate side product of failed integration, we quantified autointegration events in ledgf$^{-/-}$ and ledgf$^{+/+}$ mouse embryo fibroblasts (MEF) infected with HIV-Luc. LEDGF is a nuclear factor, which tethers the PIC to genomic DNA and plays a crucial role in chromosomal integration (M. C. Shun et al., Genes Dev 21, 1767 (2007); M. Llano et al., Science 314, 461 (2006)). Although HIV-Luc infection of ledgf$^{-/-}$ cells was barely detectable compared to ledgf$^{+/+}$ MEF, autointegration did not significantly change in ledgf$^{-/-}$ MEF (IN is fully catalytically active in ledgf$^{-/-}$ cells within the PIC (M. C. Shun et al., Genes Dev 21, 1767 (2007)) (FIG. 3G). Therefore autointegration is not an obligate side effect of decreased chromosomal DNA integration. LEDGF and the SET complex did not coimmunoprecipitate in infected cells and recombinant IN and SET also did not coprecipitate.

Our results collectively indicate that the SET complex suppresses autointegration rather than augments chromosomal integration. In support of this, individual knockdown of TREX1 or APE1, two other SET complex components, also significantly increased autointegration (FIG. 3H). Just as NM23-H1 knockdown enhanced autointegration, overexpressing NM23-H1 in an NM23-H1 defective human breast cancer cell line (MDA-MB-435) suppressed HIV-1 autointegration by 2-fold ($p<0.001$) but had no effect on reverse transcription (FIG. 3I).

BAF can augment HIV-1 integration in vitro (H. Chen, A. Engelman, Proc Natl Acad Sci USA 95, 15270 (1998)) and in cells (J. M. Jacque and M. Stevenson, Nature 441, 641 (2006)), although its overall importance during virus infection is controversial (J. M. Jacque and M. Stevenson, Nature 441, 641 (2006); M. C. Shun et al., J Virol 81, 166 (2007)). To determine whether BAF regulates autointegration, lysates prepared from HIV-Luc-infected control and BAF knockdown cells were assayed by auto-PCR. BAF knockdown was efficient (92% protein knockdown) and reduced luciferase activity about 2-fold (FIGS. 3L and 3M), but had no effect on autointegration (FIG. 3N). Therefore, although we cannot exclude a role for BAF in suppressing autointegration, it is unlikely to be the dominant mechanism through which BAF regulates HIV-1 infection.

SET and NM23-H1 Associate with HIV-1 DNA in the Cytoplasm

Autointegration product formation peaked in parallel with the late RT product (FIG. 3B), suggesting that autointegration occurs in the cytoplasm. In fact, 68% of autointegrants at their peak 10 hpi were in cytoplasmic rather than nuclear lysates (FIG. 3O). We therefore predicted that the SET complex would associate with HIV-1 reverse transcripts in the cytoplasm. The ability of SET complex and control antibodies to capture HIV-1 cDNA from cytoplasmic lysates 6 hpi was analyzed (FIG. 3J). IN and matrix (MA) antibodies captured 7.7% and 4.3% of cytoplasmic HIV-1 DNA, respectively, as assessed by qPCR. LEDGF antibody did not pull down a significant amount of HIV-1 DNA, in contrast to a previous report (M. Llano et al., J Virol 78, 9524 (2004)). SET and NM23-H1 antibodies pulled down 2.4% and 3.1% of input HIV-1 DNA, respectively, significantly more than rabbit IgG control ($p<0.005$ and $p<0.001$, respectively). The direct association of SET complex proteins with HIV-1 DNA in the cytoplasm early in infection further supports its role in preventing autointegration.

The SET Complex Suppresses Autointegration through its Role in BER

We next wanted address understand how the SET complex might recognize HIV-1 DNA and interfere with autointegration. Viral DNA in the PIC is accessible to exogenously introduced endonucleases (M. D. Miller et al., J Virol 71, 5382 (1997); B. Bowerman et al., Genes Dev 3, 469 (1989); H. Chen et al., J Biol Chem 274, 17358 (1999)), so a direct interaction between SET complex proteins and HIV-1 DNA seemed plausible. The SET complex contains 3 DNases—the BER apurinic endonuclease APE1, a DNA nicking endonuclease NM23-H1, which also catalyzes the exchange of dNDPs and dNTPs, and a 5'-3' exonuclease TREX1, which may serve as a BER proofreading endonuclease (M. Hoss et al., Embo J 18, 3868 (1999)).

We hypothesized that the presumed BER function of the SET complex, which has not formally been demonstrated, was related to its role in blocking HIV-1 autointegration. One of the roles of BER is to repair misincorporated deoxyuridine in DNA that occurs by utilizing dUTP in place of dTTP or by spontaneous deamination of incorporated cytosines, which is enhanced under oxidative conditions. For HIV-1 this represents a particular problem because reverse transcriptase (RT) does not effectively distinguish dUTP from dTTP and the dUTP/dTTP ratio is especially high in primary immune cells susceptible to HIV-1 infection (S. Aquaro et al., Antiviral Res 55, 209 (2002)). Moreover, the host cytidine deaminase APOBEC3G (A3G) can attack the minus strand during reverse transcription in immune cells (A. M. Sheehy et al., Nat Med 9, 1404 (2003); D. Harris and A. Engelman, J Biol Chem 275, 39671 (2000); Y. L. Chiu and W. C. Greene, Annu Rev Immunol 26, 317 (2008)).

HIV-1 has a number of known strategies for preventing or removing inappropriate deoxyuridine from its reverse transcript. UNG2, the major host uracil DNA glycosylase and the first BER enzyme required to remove misincorporated uracils before APE1 cleaves 5' to the abasic residue, binds to Vpr and is incorporated into virions through an interaction with IN (M. Bouhamdan et al., J Virol 70, 697 (1996)). dUTPase and APE1 may also be packaged into virions (B. Yang et al., J Biol Chem 282, 11667 (2007)), although this is less certain. HIV-1 protects itself from A3G by Vif, which ubiquitylates A3G to mark it for proteosomal degradation (A. M. Sheehy et al., Nat Med 9, 1404 (2003); X. Yu et al., Science 302, 1056 (2003); Y. L. Chiu and W. C. Greene, J Biol Chem 281, 8309 (2006)). Our results heretofore were obtained using virus grown and propagated in A3G deficient cells (293T and HeLaCD4), so the SET complex is important for blocking autointegration even in the absence of A3G activity.

Figure 4:
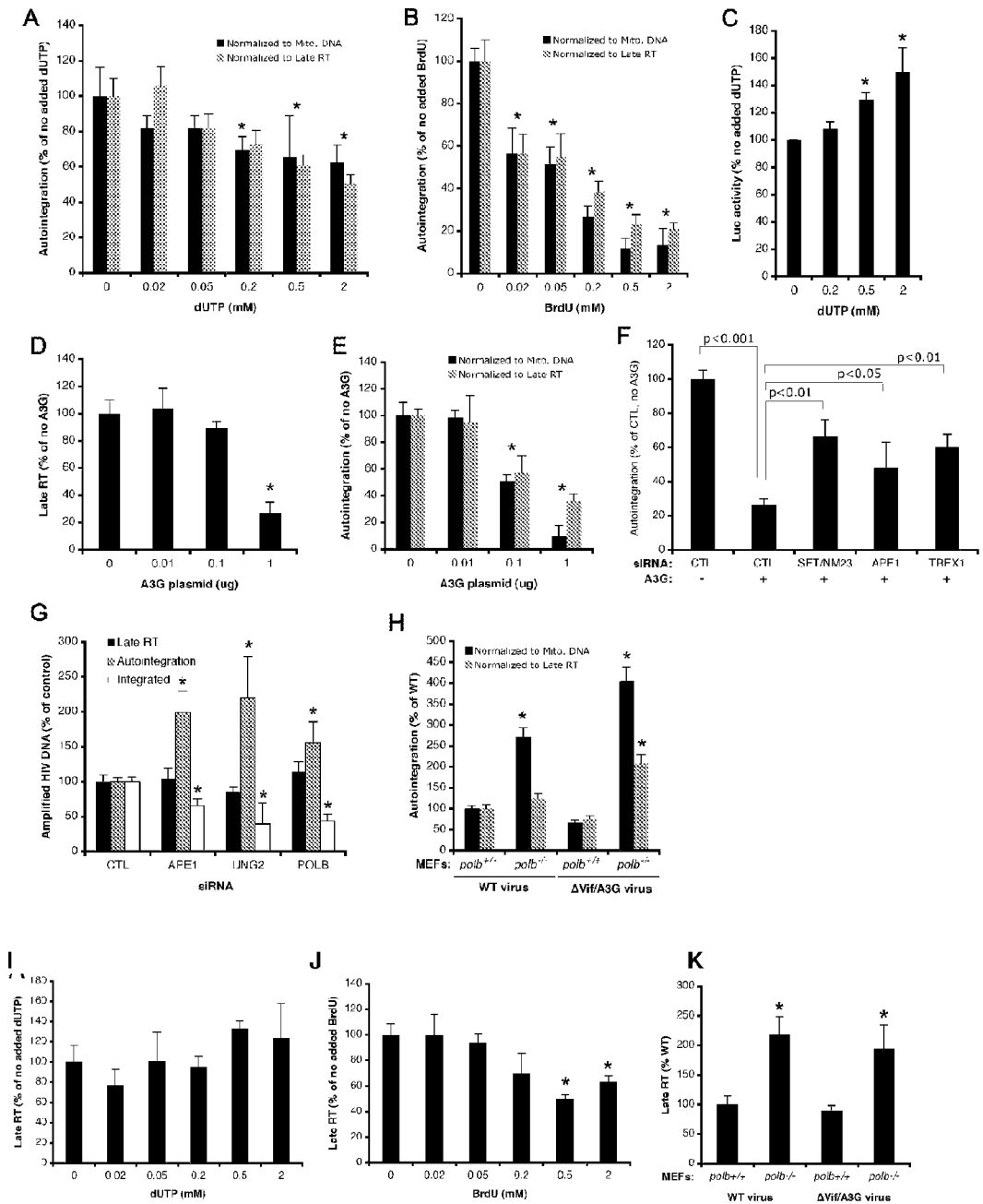
FIG. 4 demonstrates that the SET complex suppresses autointegration through BER.
Figure 4:
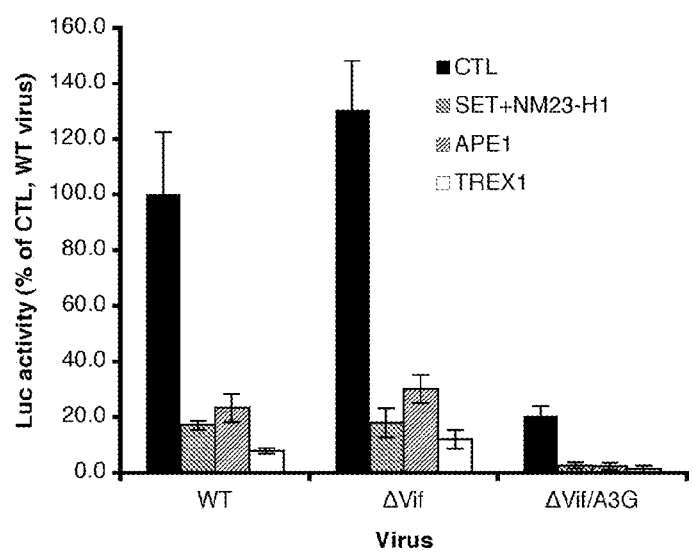

To determine whether the postulated BER role of the SET complex might be important in its function as a barrier to autointegration, the effect on autointegration of enhancing uracil incorporation into HIV-1 cDNA was analyzed. Cells grown in medium supplemented with dUTP or BrdU were infected and then processed for qPCR assays; late RT and auto-PCR products were assessed 10 hpi, and autointegration was normalized to either mitochrondrial DNA or late RT (FIGS. 4I and 4J). Late RT products were not affected by dUTP, but were diminished at higher concentrations of BrdU. With increasing dUTP or BrdU, autointegration decreased, even when normalized to late RT levels (FIGS. 4A and 4B). Virus luciferase activity 48 hpi in the presence of dUTP or BrdU conversely increased (FIG. 4C). Another mechanism of enhancing BER DNA substrate is by increasing cytosine deamination, which was accomplished by packaging increasing amounts of A3G into ΔVif virus. As expected (K. N. Bishop et al., J Virol 80, 8450 (2006); R. K. Holmes et al., J Biol Chem 282, 2587 (2007); J. H. Simon and M. H. Malim, J Virol 70, 5297 (1996); U. von Schwedler et al., J Virol 67, 4945 (1993)), when present at high concentrations, A3G diminished late RT (FIG. 4D). However, as was seen with increased misincorporation due to dUTP or BrdU, autointegration decreased with increasing A3G, even when normalized to late RT (FIG. 4E). Knockdown of SET complex components inhibited infection with ΔVif virus as efficiently as Vif+ virus and further suppressed the low levels of infection that occurred after infection with ΔVif virions containing A3G (FIG. 4L). Moreover, knockdown of SET/NM23-H1, APE1 or TREX1 enhanced autointegration when cells were infected with ΔVif virus containing A3G (FIG. 4F). Therefore, the SET complex may mobilize in the cytoplasm to misincorporated or mismatched viral cDNA sites and protect these (and possibly other nearby regions of the HIV-1 genome) from IN-mediated autointegration.

If the BER function of the SET complex is critical for its role as a barrier to autointegration, then upstream and downstream enzymes in short-patch BER might also inhibit autointegration. UNG2 excises misincorporated uracils to create an abasic site. APE1 then cleaves 5' of the abasic site, forming a gap that is filled in by DNA polymerase β (POLB) and sealed by DNA ligase III (T. Lindahl et al., DNA Repair (Amst) 3, 1522 (2004)). These other BER enzymes are not in the SET complex. To determine whether other short-patch BER pathway components protect against autointegration, we knocked down UNG2 and POLB and analyzed the formation of stage-specific HIV-1 DNA products. As for APE1, knockdown of either UNG2 or POLB inhibited chromosomal integration and enhanced autointegration (FIG. 4G). Similarly, polb$^{-/-}$ MEF supported significantly more autointegration than polb$^{+/+}$ MEF (FIG. 4H). When U:G mismatches requiring BER repair were increased by infecting with ΔVif/A3G virus instead of HIV-Luc (Vif$^+$/A3G$^-$), the effect of POLB on blocking autointegration was more pronounced (FIG. 4H). Of note, polb$^{-/-}$ cells produced ~2-fold more late RT products than polb$^{+/+}$ cells (FIG. 4K), indicating an unknown role of POLB in HIV-1 reverse transcription or stability of the late RT product.

Discussion

These results identify the SET complex as a cytoplasmic barrier to autointegration, acting through its presumed role in BER. Knockdown of 5 SET complex proteins or of more proximal and distal short-patch BER enzymes increased autointegration and decreased chromosomal integration. Moreover, the SET complex proteins SET and NM23-H1 associate with HIV-1 DNA in the cytoplasm. Although there are reports that other DNA repair factors either facilitate or inhibit HIV-1 infection, most of these have been postulated to influence 2-LTR circle formation or 5' gap repair and to act in the nucleus (K. Yoder et al., Proc Natl Acad Sci USA 103, 4622 (2006); A. Lau et al., Embo J 23, 3421 (2004); K. E. Yoder and F. D. Bushman, J Virol 74, 11191 (2000); R. Daniel et al., Science 284, 644 (1999)).

Figure 5:
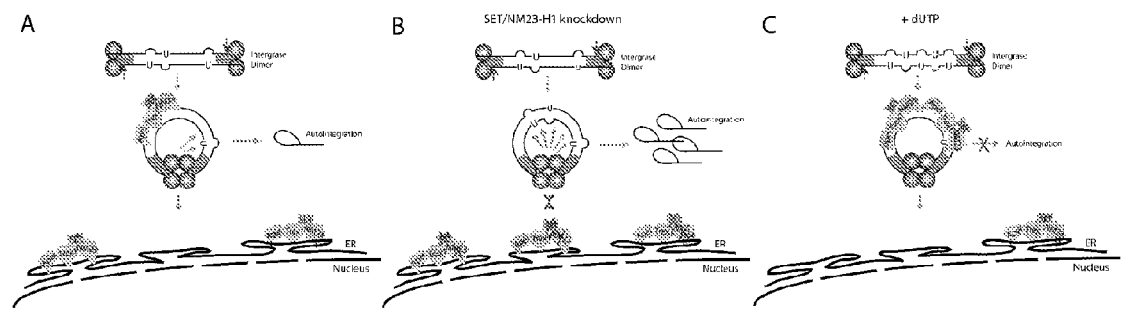
FIG. 5 depicts a schematic drawing of a proposed, non-limiting, model for how the SET complex blocks autointegration. The SET complex binds to mismatched or abasic sites in HIV-1 DNA as soon as reverse transcription is complete to protect them and nearby sites from autointegration (FIG. 5A). Without wishing to be bound by theory, it is proposed that when the SET complex is disrupted or functionally impaired by knocking down one of its components, HIV-1 DNA is vulnerable to autointegration (FIG. 5B). Enhancing HIV-1 uracil incorporation or DNA mismatches by increasing dUTP or BrdU concentration, or infection with ΔVif/A3G virus, enhances SET complex binding, which reduces autointegration (FIG. 5C).

While not wishing to be bound by theory, two models for the mechanism by which the SET complex suppresses HIV-1 autointegration are envisaged. One model (FIG. 5), which we favor, is that the SET complex inhibits autointegration by binding to misincorporated or abasic sites on HIV-1 cDNA and, while repairing them, protects them (and possibly nearby sites) from self-attack. HIV-1 may be especially vulnerable to misincorporations/mismatches that require BER since its RT misincorporates dUTP for dTTP and the HIV-1 reverse transcript is susceptible to attack by the host A3G cytidine deaminase. HIV-1 has several known strategies for exploiting the host BER machinery—HIV Vpr and IN bind UNG2 and IN facilitates its packaging into virions (M. Bouhamdan et al., J Virol 70, 697 (1996); S. Priet et al., J Biol Chem 278, 4566 (2003)), and HIV Vif directs the degradation of A3G. Although APE1 nicking has previously been proposed as a threat to HIV-1 cDNA (B. Yang et al., J Biol Chem 282, 11667 (2007)), our results indicate that within the SET complex, APE1 plays a protective role, likely by participating in the repair of mismatched and abasic sites.

Knocking down multiple SET complex proteins enhanced autointegration. Further investigation would be needed to elucidate the molecular details of how the SET complex interacts with HIV-1 cDNA, and whether each of the three nuclease activities of the complex is essential for its function. The other SET complex proteins (SET, pp32, and HMGB2) in BER and/or blocking autointegration might be required for maintaining the integrity of the complex, recognizing the mismatched or damaged base (HMGB2), or regulating the repair process (SET). In addition to its nuclease function, NM23-H1 is a nucleoside diphosphate kinase that catalyzes the exchange of dNDPs for dNTPs and therefore potentially regulates the pool of bases available for reverse transcription and/or repair.

Again while not wishing to be bound by theory, another model, not mutually exclusive, posits that the SET complex might act by promoting HIV-1 DNA access to cell chromosomes. SET is a histone H2B chaperone that is believed to increase DNA accessibility by removing histone H2 dimers from nucleosomes. Because we did not observe any change in chromosomal HIV-1 integration site preference in SET/NM23-H1 knockdown cells, or SET binding to IN or LEDGF, a dominant direct role in chromosomal integration seems less likely. However, we do not know whether the SET complex remains associated with the PIC during and after nuclear import. Since the complex shuttles back and forth to the nucleus, this remains a distinct possibility. SET complex proteins are also known to regulate histone modifications and transcriptional activation from some promoters, suggesting potential post-integration effects. However, knocking down SET and NM23-H1 did not alter transcription from the HIV-1 LTR of a transfected plasmid, making this less likely. Nonetheless, it will be worthwhile to investigate potential nuclear roles for the SET complex in the HIV-1 life cycle.

Methods

Cell Lines: Cells were grown in Dulbecco's modified Eagle's medium (DMEM) (Gibco) supplemented with 10% heat-inactivated fetal bovine serum (FBS) at 37° C. and 5% $CO_2$ unless specified otherwise. HeLaCD4 and TZM-b1 cells were obtained form the NIH AIDS Reagent and Reference Program. MDA-MB-435 cell lines, C100 and H1-117, were a kind gift of Patricia Steeg (NCI) C. E. Horak et al., Cancer Res 67, 7238 (2007). Chicken DF1 cells (a gift of James Cunningham, Harvard Medical School) were propagated in DMEM/10% FBS, 100 U/mL penicillin G sodium, and 100 µg/mL streptomycin sulfate. The ledgf+/+ and ledgf−/− MEF used in this study will be described elsewhere. polb+/+ and polb−/− MEF, a kind gift of Sam Wilson (NIH), (R. W. Sobol et al., Nature 379, 183 (1996)) were grown in DMEM/10% FBS, 80 µg/ml Hygromycin B (Invitrogen), 1× GlutaMax (Gibco) at 34° C. in 10% $CO_2$.

Virus production and infection: HIVIIIB was propagated as described previously (A. L. Brass et al., Science 319, 921 (2008)). HIV-Luc and MLV-Luc constructs were described previously (M. C. Shun, J Virol 81, 166 (2007)). SIV-Luc was kindly provided by Ned Landau (NYU) (B. Schrofelbauer, et al., J Virol 80, 5984 (2006)). Viral supernatants were produced from transfected 293T cells as described(M. C. Shun, J Virol 81, 166 (2007)). ASV-Luc (24 mL) was produced from DF1 cells plated at 2×106/10 cm dish the day prior to co-transfecting with 15 µg pRIAS-Luc and 10 µg pHCMV-G (J. Yee et al., Proc. Natl. Acad. Sci. USA 91, 9564 (1994)) using Fugene 6 as recommended by the manufacturer. Virus was harvested over 3 successive days and concentrated approximately 32-fold by ultracentrifugation prior to use. HIV-LucΔ-Vif and pCMV-APOBEC3G plasmids were kindly provided by Dana Gabuzda (DFCI). All HIV-1 viruses were titered using p24 ELISA. Infections were performed using an MOI of 1 for 6-8 h before replacing viral supernatants with fresh medium. Luc activity was assayed 48 hpi as described (M. C. Shun, J Virol 81, 166 (2007)). Briefly, cells in 12-well plates were lysed with 250 uL 1× Passive Lysis Buffer (Promega) for 15 minutes at room temperature. Cell lysates were collected as supernatants after a quick spin to pellet cell debris. Luc activity was measured using Luc Assay Reagent (Promega) substrate in a Synergy 2 luminometer (BioTek). Protein levels in cell lysates were determined by BCA assay (Thermo Scientific). β-galactosidase activity was measured using Gal Screen (TROPIX). For experiments that measured stage-specific HIV-1 DNAs, viral supernatants were pretreated with 40 U/mL Turbo DNase (Ambion) at 37° C. for 1 h. Cells were infected using DNase-treated viruses, and DNA was isolated using the Hirt method (B. Hirt, J Mol Biol 26, 365 (1967)) at specified times post infection.

Plasmids, siRNAs, transfection: SET cDNA was PCR amplified from pET26b-SET (P. J. Beresford et al., J Biol Chem 276, 43285 (2001)) using primers containing BamHI and XhoI restriction sites and a FLAG tag on the C-termal end. The resultant fragment was subsequently cloned into pcDNA3 (Invitrogen) to generate pcDNA-SET-FLAG for expression in mammalian cells. pcDNA-SET-in-FLAG (insensitive to SET siRNA) was constructed based on pcDNA-SET-FLAG with silent mutations introduced using the QuikChange kit (Statagene). Primers used were:

SEQ ID NO: 46: forward primer:
5'CCAACCACGACGGCGCGGATGAAACGTCTGAGAAAGAACAGC-3';
and SEQ ID NO: 47: reverse primer:
5'-GCTGTTCTTTCTCAGACGTTTCATCCGCGCCGTCGTGGTTGG-3'.

pRIAS-Luc, which encodes for single-round (replication-incompetent) ASV carrying the Luc reporter gene (ASV- Luc), was built by amplifying Luc sequences from pNLX.Luc (R−) (R. Lu et al., J. Virol. 78, 12735 (2004)) with primers:

SEQ ID NO: 48:
AE675 (5'-GGTACTATCGATAAAGCCACCATGGAAG)
and

SEQ ID NO: 49:
AE3292 (5'-CTAGATCGATTACACGGCGATCTTTCC), digesting with Cla I, and ligation to Cla I-digested pRIAS (C. M. A. Chen et al., Dev. Biol. 214, 370(1999)).

siRNAs were transfected using Oligofectamine (Invitrogen) following manufacturer's protocols. Cells were transfected twice in two consecutive days and were infected on the third day. DNAs were transfected using Lipofectamine 2000 (Invitrogen) following manufacturer's protocols. siRNAs were purchased from Dharmacon. Catalog numbers are given for siRNAs pre-designed by Dharmacon and a single siRNA that gave the best knockdown from each set of 4 was labeled as 'preferred' and used in this study. An equal molar mix of two TREX1 siRNAs was used to maximize knockdown. All sequences correspond to sense strand sequence of the target gene.

SET siRNA:
SEQ ID NO: 1:
5'-GGCCGACGAGACCUCAGAA-3' (Z. Fan, P. J. Beresford, D. Y. Oh, D. Zhang, J. Lieberman, Cell 112, 659 (2003))

NM23-H1 siRNA:
SEQ ID NO: 2:
5'-GGAUUCCGCCUUGUUGGGUC-3' (Z. Fan, P. J. Beresford, D. Y. Oh, D. Zhang, J. Lieberman, Cell 112, 659 (2003))

TREX1 siRNAs:
SEQ ID NO: 3:
5'-CCAAGACCATCTGCTGTCA-3';

SEQ ID NO: 4:
5'-ACAATGGTGACCGCTACGA-3' (D. Chowdhury et al., Mol Cell 23, 133 (2006))

pp32 siRNA:
SEQ ID NO: 5:
5'-GGAGGCCCCUGACUCGGAU-3'

APE1 siRNAs:
SEQ ID NO: 6::
5'-CAAAGUUUCUUACGGCAUA-3' (cat# J-010237; preferred);

SEQ ID NO: 7:
5'-GAGACCAAAUGUUCAGAGAUU-3';

SEQ ID NO: 8:
5'-CUUCGAGCCUGGAUUAAGA-3';

SEQ ID NO: 9:
5'-UAACAGCAUAUGUACCUAA-3'

POLB siRNA:
SEQ ID NO: 10:
5'-UCAAUGAGUACACCAUCCG-3' (Y. Y. Polosina, et al., DNA Repair (Amst) 3, 1469 (2004))

UNG2 siRNA
SEQ ID NO: 11:
5'-GCUCAUCGCUUGCAAACAG-3'; (cat# J-008515)

SEQ ID NO: 12:
5'-CUACAGACCUUCCGCGACU;

SEQ ID NO: 13:
5'-CAUAAACAGUACUUCCUUG-3';

SEQ ID NO: 14:
5'-GAAUCCCGCUGUAAGCUGC-3' (preferred)

CD4 siRNA:
SEQ ID NO: 50:
5'-GAUCAAGAGACUCCUCAGU-3' (C. D. Novina et al., Nat Med 8, 681 (2002))

BAF-c siRNA:
SEQ ID NO: 51:
5'-GAAGCUGCACGUAAGGGGU-3' (M. C. Shun et al., J Virol 81, 166 (2007))

BAF siRNA:
SEQ ID NO: 52:
5'-GAAGCUGGAGGAAAGGGG-3' (M. C. Shun et al., J Virol 81, 166 (2007))

Non-targeting siRNA #1:
SEQ ID NO: 53:
5'-UAGCGACUAAACACAUCAA-3' (cat# D-001210-01):

Integration site sequence analysis Human (build 36.1, UCSC hg18 release) genomic sequence and HIV-1NL4-3 sequence databases were used for integration site sequence analysis, which was done as described (M. C. Shun et al., Genes Dev 21, 1767 (2007)).

PIC isolation, HIV DNA immunoprecipitation (IP), antibodies. HIV PICs were isolated as described (M. C. Shun et al., Genes Dev 21, 1767 (2007); H. Chen, et al., J Biol Chem 274, 17358 (1999)) with slight modifications. Briefly, HeLaCD4 cells grown on 10 cm plates (80% confluent) were infected with DNase-treated HIV-Luc. Each plate provided enough cells for two IP experiments. Cells were washed with cold Buffer K−/− (20 mM HEPES, pH 7.6, 150 mM KCl, 5 mM MgCl2) twice 6 hpi and lysed by rocking at room temperature for 8 min 0.5 mL Buffer K+/+ (Buffer K−/− containing 1× Protease inhibitors (EDTA-free, Roche), 0.025% digitonin, 1 mM DTT) per 10 cm plate. Supernatants were obtained following successive centrifugations at 1,500×g for 4 mM at 4° C. and 15,000×g for 1 min at 4° C. Resultant cytoplasmic PIC extracts were incubated with specific antibodies that were pre-bound to protein A or G agarose beads overnight. Beads were washed the next morning with 100 mM KCl wash buffer twice (20 mM Tris7.4, 0.2 mM EDTA, 100 mM KCl, 5 mM □-mercaptoethanol, 1× protease inhibitors complete, 10% Glycerol) and again with the same buffer containing 300 mM KCl before elution with 2×100 μL 200 mM glycine (pH 3). Eluates were neutralized by adding 2 μL of 1.5 M Tris-HCl (pH 8.8) before phenol/chloroform/iodoacetamide extraction and DNA precipitation. HIV-1 DNA in the IP was quantified using qPCR with late RT primers (MH531/MH532). Antibodies for IP were: anti-IN (rabbit, affinity purified) (P. Cherepanov et al., FASEB J 14, 1389 (2000)), anti-MA (mouse 3H7) (C. W. Lin, A. Engelman, J Virol 77, 5030 (2003)), anti-SET (rabbit, affinity purified) (P. J. Beresford et al., J Biol Chem 276, 43285 (2001)), anti-NM23-H1 (rabbit, Santa Cruz #sc343) and anti-LEDGF/p75

(mouse, BD Transduction #611714). Antibodies used for immunoblot were anti-Apel (rabbit, this study), anti-pp32 (mouse) (P. J. Beresford et al., J Biol Chem 276, 43285 (2001)), anti-UNG2 (rabbit, ProSci #3859), anti-POLB (rabbit, Abcam #ab26343), anti-BAF (rabbit, a kind gift of Katherine Wilson (John Hopkins University School of Medicine) (M. Segura-Totten, A. K. Kowalski, R. Craigie, K. L. Wilson, J Cell Biol 158, 475 (2002)) and anti-BrdU-FITC (mouse, Abcam #7796).

Quantitative PCR, Auto-PCR HIV-1 late RT, integrated DNA, and 2-LTR circles were quantified as previously described (M. C. Shun et al., Genes Dev 21, 1767 (2007); S. L. Butler et al., Nat Med 7, 631 (2001)). Briefly, mitochondrial DNA, late RT and 2-LTR circles in extrachromosomal DNA fractions were analyzed by qPCR using MIT+/MIT−, MH531/MH532 and AE2948/AE2949 primers, respectively (sequences below). β-Globin DNA was similarly measured in chromosomal DNA fractions using β-Globin+/β-Globin− primers (sequences below). Integrated HIV DNA was also measured in chromosomal fractions, but by Alu-PCR followed by nested qPCR using AE989/AE990 primers (sequences below). Autointegration products were measured using a two-step nested PCR: Step 1 is a semiquantitative PCR using 200 ng extrachromosomal DNA, 1× PCR buffer, 1.5 mM MgCl2, 0.2 µM of each primer (PBS−, NY200/A+, NY199/B−), 0.2 mM dNTP and 1.5 U Platinum Taq polymerase (Invitrogen) in a 25 µL reaction volume. PCR program was 94° C./5 min, 24 cycles of 95° C./30 s-60° C./30 s-72° C./3 min, then 72° C./7 min. PCR products from Step 1 were diluted 1:100 for use in Step 2. Step 2 was a qPCR assay using AE989/AE990 primers (M. C. Shun et al., Genes Dev 21, 1767 (2007)).

Primer sequences:

```
SEQ ID NO: 15: MIT+:
5'-GACGTTAGGTCAAGGTGTAG-3'

SEQ ID NO: 16 MIT-:
5'-CAACTAAGCACTCTACTCTC-3'

SEQ ID NO: 17 MH531 (late RT forward):
5'-TGTGTGCCCGTCTGTTGTGT-3'

SEQ ID NO: 18 MH532 (late RT reverse):
5'-GAGTCCTGCGTCGAGAGAGC-3'

SEQ ID NO: 19 AE2948 (2-LTR forward):
5'-AACTAGGGAACCCACTGCTTAAG-3'

SEQ ID NO: 20 AE2949 (2-LTR reverse):
5'-TCCACAGATCAAGGATATCTTGTC-3'

SEQ ID NO: 21 β-Globin+:
5'-GAAGAGCCAAGGACAGGTAC-3'

SEQ ID NO: 22 β-Globin-:
5'-AAGCAATAGATGGCTCTGCC-3'

SEQ ID NO: 23 PBS-:
5'-TTTCCGGTCCCTGTTCGGGCGCCA-3'

SEQ ID NO: 24 Alu:
5'-TCCCAGCTACTCGGGAGGCTGAGG-3'

SEQ ID NO: 25 AE989 (R):
5'-TCTGGCTAGCTAGGGAACCCA-3'

SEQ ID NO: 26 AE990 (U5):
5'-CTGACTAGGATGGTCTGAGG-3'

SEQ ID NO: 27 NY199/primer B-:
5'-CTACCTTGTTATGTCCTGCTTG-3'

SEQ ID NO: 28 NY200/primer A+:
5'-CTCTACAGCACTTGGCACTAGC-3'
```

Deoxynucleotide treatment dUTP (Roche) and BrdU (Sigma) were added at indicated concentrations to DMEM/10% FBS medium at least 12 h before infection. The same concentration was maintained in the medium until the cells were harvested.

We claim:

1. A method of decreasing retroviral nucleic acid integration into a host cell genome, said method comprising contacting a cell infected with a retrovirus with an inhibitor of one or more components of the SET complex, wherein said inhibitor decreases retroviral nucleic acid integration and wherein said inhibitor is a nucleic acid inhibitor comprising a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:9.

2. The method of claim 1, wherein the inhibitor of one or more components of the SET complex increases autointegration of a retroviral nucleic acid.

3. The method of claim 1, wherein the retrovirus is a human immunodeficiency virus (HIV).

4. A method for the treatment of a retroviral infection in a subject in need thereof, the method comprising administering to a subject in need an effective amount of a composition comprising an inhibitor of one or more components of the SET complex, wherein said inhibitor decreases retroviral infection in said subject, and wherein said inhibitor is a nucleic acid inhibitor that comprises a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:9.

5. The method of claim 4, wherein the retroviral infection is a human immunodeficiency virus (HIV) infection.

* * * * *

SEQUENCE LISTING

```
<160> NUMBER OF SEQ ID NOS: 54

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
ggccgacgag accucagaa                                                  19

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
ggauuccgcc uuguugguc                                                  19

<210> SEQ ID NO 3
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ccaagaccat ctgctgtca                                                19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
acaatggtga ccgctacga                                                19

<210> SEQ ID NO 5
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
ggaggccccu gacucggau                                                19

<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
caaaguuucu uacggcaua                                                19

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gagaccaaau guucagagau u                                             21

<210> SEQ ID NO 8
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
cuucgagccu ggauuaaga                                                19

<210> SEQ ID NO 9
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 9
uaacagcaua uguaccuaa                                                    19

<210> SEQ ID NO 10
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
ucaaugagua caccauccg                                                    19

<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
gcucaucgcu ugcaaacag                                                    19

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
cuacagaccu uccgcgacu                                                    19

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
cauaaacagu acuuccuug                                                    19

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
gaaucccgcu guaagcugc                                                    19

<210> SEQ ID NO 15
<211> LENGTH: 20
<212> TYPE: DNA
<213> ORGANISM: Artificial Sequence
```

-continued

<220> FEATURE:
<223> OTHER INFORMATION: Description of Artificial Sequence: Synthetic
      primer

<400> SEQUENCE: 15
gacgttaggt caaggtgtag                                                 20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
caactaagca ctctactctc                                                 20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgtgtgcccg tctgttgtgt                                                 20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gagtcctgcg tcgagagagc                                                 20

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aactagggaa cccactgctt aag                                             23

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tccacagatc aaggatatct tgtc                                            24

<210> SEQ ID NO 21
<211> LENGTH: 20
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 21
gaagagccaa ggacaggtac                                              20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aagcaataga tggctctgcc                                              20

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tttccggtcc ctgttcgggc gcca                                         24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tcccagctac tcgggaggct gagg                                         24

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tctggctagc tagggaaccc a                                            21

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ctgactagga tggtctgagg                                              20

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic

```
                                    primer

<400> SEQUENCE: 27
ctaccttgtt atgtcctgct tg                                              22

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ctctacagca cttggcacta gc                                              22

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ttagcctttc cacctacaat cc                                              22

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ttagcccttc caaaagatta gt                                              22

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ttagcccttc caggagaaag ag                                              22

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ttagcccttc cagtctccat ag                                              22

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 33
ttagcccttc caaaagcaaa ga                                              22

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ttagcccttc cagaaagtac ta                                              22

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ttagcccttc cactaatcca aa                                              22

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ttagcccttc caggagaaag ag                                              22

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ttagcccttc catatagtta gt                                              22

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ttagcccttc caggcagtag ta                                              22

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 39
ttagcccttc caaagtagac cc                                              22

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ttagcccttc cagtctccat ag                                              22

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ttagcccttc cagtaataac aa                                              22

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tgaataaaga aacaaggtag                                                 20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
tcctctggaa aacaaggtag                                                 20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
actaatccaa aacaaggtag                                                 20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
```
gggcaagaaa aacaaggtag          20

<210> SEQ ID NO 46
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ccaaccacga cggcgcggat gaaacgtctg agaaagaaca gc          42

<210> SEQ ID NO 47
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gctgttcttt ctcagacgtt tcatccgcgc cgtcgtggtt gg          42

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ggtactatcg ataaagccac catggaag          28

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ctagatcgat tacacggcga tctttcc          27

<210> SEQ ID NO 50
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
gaucaagaga cuccucagu          19

<210> SEQ ID NO 51
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51

```
gaagcugcac guaaggggu                                           19

<210> SEQ ID NO 52
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
gaagcuggag gaaagggg                                            18

<210> SEQ ID NO 53
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
uagcgacuaa acacaucaa                                           19

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(21)
<223> OTHER INFORMATION: a, c, t, g, unknown or other

<400> SEQUENCE: 54
aannnnnnnn nnnnnnnnnn ntt                                      23
```